(12) United States Patent
Gross et al.

(10) Patent No.: US 12,087,402 B2
(45) Date of Patent: Sep. 10, 2024

(54) METHODS, SYSTEMS AND PROCESSES OF DETERMINING TRANSMISSION PATH OF INFECTIOUS AGENTS

(71) Applicant: KONINKLIJKE PHILIPS N.V., Eindhoven (NL)

(72) Inventors: Brian David Gross, North Andover, MA (US); Thomas Chou, Andover, MA (US); Saeed Babaeizadeh, Arlington, MA (US); Pradyumna Dutta, Bedford Corners, NY (US); Andrew Arthur, Hollis, NH (US); Henry Lin, Quincy, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1438 days.

(21) Appl. No.: 15/772,389

(22) PCT Filed: Oct. 28, 2016

(86) PCT No.: PCT/IB2016/056497
§ 371 (c)(1),
(2) Date: Apr. 30, 2018

(87) PCT Pub. No.: WO2017/072707
PCT Pub. Date: May 4, 2017

(65) Prior Publication Data
US 2018/0314793 A1    Nov. 1, 2018

Related U.S. Application Data

(60) Provisional application No. 62/248,555, filed on Oct. 30, 2015.

(51) Int. Cl.
| | |
|---|---|
| *G16B 30/00* | (2019.01) |
| *C12Q 1/6827* | (2018.01) |
| *C12Q 1/6869* | (2018.01) |
| *C12Q 1/689* | (2018.01) |
| *G06F 17/18* | (2006.01) |
| *G16B 10/00* | (2019.01) |
| *G16B 20/00* | (2019.01) |

(Continued)

(52) U.S. Cl.
CPC ......... *G16B 30/00* (2019.02); *C12Q 1/6827* (2013.01); *C12Q 1/6869* (2013.01); *C12Q 1/689* (2013.01);
(Continued)

(58) Field of Classification Search
CPC ........ G16B 30/00; G16B 30/10; G16B 40/20; G16B 20/00; G16B 10/00; G16B 50/00;
(Continued)

(56) References Cited

U.S. PATENT DOCUMENTS

2002/0120408 A1    8/2002  Kreiswirth et al.
2007/0131862 A1*   6/2007  Cowan ................ G01N 21/274
                                                250/339.09
(Continued)

FOREIGN PATENT DOCUMENTS

| JP | 2004234459 A | 8/2004 |
| JP | 2014146155 A | 8/2014 |

OTHER PUBLICATIONS

Fahey, Marie E., et al. "GPS-Prot: a web-based visualization platform for integrating host-pathogen interaction data." BMC bioinformatics 12.1 (2011): 1-13. (Year: 2011).*

(Continued)

*Primary Examiner* — Larry D Riggs, II
*Assistant Examiner* — Guozhen Liu

(57) ABSTRACT

Provided herein are computer implemented methods, systems and processes for determining a transmission metric or transmission path for related pathogens. Also provided herein is a non-transitory computer-readable storage medium with an executable program stored thereon, which program is configured to instruct a microprocessor to generate a transmission path for related pathogens.

15 Claims, 20 Drawing Sheets

(51) Int. Cl.
G16B 30/10 (2019.01)
G16B 40/20 (2019.01)
G16B 50/00 (2019.01)

(52) U.S. Cl.
CPC ............ *G06F 17/18* (2013.01); *G16B 10/00* (2019.02); *G16B 20/00* (2019.02); *G16B 30/10* (2019.02); *G16B 40/20* (2019.02); *G16B 50/00* (2019.02)

(58) Field of Classification Search
CPC .... C12Q 1/6827; C12Q 1/6869; C12Q 1/689; G06F 17/18
See application file for complete search history.

(56) References Cited

U.S. PATENT DOCUMENTS

| | | |
|---|---|---|
| 2008/0147443 A1 | 6/2008 | Koetter et al. |
| 2008/0183396 A1 | 7/2008 | Rinaldo et al. |
| 2010/0288295 A1 | 11/2010 | Goto |
| 2015/0234981 A1 | 8/2015 | Naidich |
| 2015/0287182 A1 | 10/2015 | Herger et al. |

OTHER PUBLICATIONS

Ypma, et al., "Unravelling transmission trees of infectious diseases by combining genetic and epidemiological data", Proceedings of the Royal Society (2012), 279; downloaded from http://rspb.royalsocietypublishing.org/, Published online Jul. 6, 2011, pp. 444-450.

O'Neil, P. D. et al., "Analyses of infectious disease data from household outbreaks by Markov chain Monte Carlo methods." Journal of the Royal Statistical Society: Series C (Applied Statistics), 2000, 49(4): 517-542.

Cai Chao-Ran et al., "Effective degree Markov-chain approach for discrete-time epidemic processes on uncorrelated networks." Physical Review E, 2014, Abstract.

* cited by examiner

FIG. 2

Sequencing analysis    Infection control                                                  User name ▾

Running sequences

[ New sequence sample input ]  ↻ Refresh

| Start time ▾ | End time | Pathogen | # of samples | Overall status | Completed | Warning | Failure | Uploaded by | Pipeline version |
|---|---|---|---|---|---|---|---|---|---|
| 05/05/2015 6:52 PM | -- | E. faecium | 15 | ▭ | 12 | 1 | 1 | Ellie Hodunk | Aurora A.00.013 |
| | | Staph. a | 12 | ▭ | 7 | 1 | 0 | Ellie Hodunk | Aurora A.00.013 |
| | | Kleb. p. | 2 | ▭ | 0 | 0 | 0 | Ellie Hodunk | Aurora A.00.013 |
| | | Pseudomonas a | 16 | ▭ | 1 | 2 | 0 | Ellie Hodunk | Aurora A.00.013 |
| 05/05/2015 4:23 PM | -- | E. faecium | 22 | ▭ | 12 | 7 | 2 | Ellie Hodunk | Aurora A.00.013 |
| | | Staph. a | 3 | ▭ | 1 | 1 | 0 | Ellie Hodunk | Aurora A.00.013 |

Completed sequences

| Start time ▾ | End time | Pathogen | # of samples | Overall status | Current step | Warning | Failure | Uploaded by | Pipeline version |
|---|---|---|---|---|---|---|---|---|---|
| 05/03/2015 8:32 AM | 05/03/2015 1:21 PM | Kleb. p. | 22 | ⊘ | 2 | 1 | 0 | John Doe | Aurora A.00.013 |
| | | Pseudomonas a | 16 | ⬇ | 12 | 1 | 4 | John Doe | Aurora A.00.013 |
| 04/21/2015 10:45 PM | 04/22/2015 4:23 AM | E. faecium | 22 | ⬇ | 16 | 1 | 6 | Jane Doe | Aurora A.00.013 |
| | | Staph. a. | 3 | ⊘ | 3 | 1 | 0 | Jane Doe | Aurora A.00.013 |

| Sequencing analysis | Infection control | | | | | | | | | | | | | | | | |
|---|---|---|---|---|---|---|---|---|---|---|---|---|---|---|---|---|---|

| | | Pseudomonas a | Kleb. p. | | | | | | | | | | | | | | |
|---|---|---|---|---|---|---|---|---|---|---|---|---|---|---|---|---|---|
| < Sequences | | 05/03/2015 – 05/03/2015<br>8:32 AM  1:21 PM | | | | | | | | | | | | | | | |

Column headers (diagonal): Basic stat, Per base seq qual, Per base seq qual score, Per base seq cont., Per seq GC cont., Per base GC cont., Per base N cont., Seq left dis., Seq dup lvl, Overrepres., km

| | | Sample date | Status | Name | MRN | Accession # | Sample source | | | | | | | | | | |
|---|---|---|---|---|---|---|---|---|---|---|---|---|---|---|---|---|---|
| ① Upload file | Running 0<br>Passed 18<br>Warning 0<br>Failed 0 | 05/03/2015 16:24 | ▣ | A | 432 | 123 | Indwelling UC | ○ | ○ | ○ | ○ | ○ | ○ | ○ | ○ | ○ | ○ |
| | | 05/02/2015 12:23 | ▣ | B | 537 | 124 | BLOOD | ○ | ○ | ● | ○ | ○ | ○ | ● | ○ | ○ | ○ |
| | | 05/01/2015 05:30 | ▣ | C | 209 | 125 | BLOOD | ○ | ○ | ○ | ○ | ○ | ○ | ○ | ○ | ○ | ○ |
| ② Alignment | Running 0<br>Passed 15<br>Warning 2<br>Failed 3 | 05/01/2015 03:18 | ✓ | D | 654 | 126 | Sputum | ○ | ● | ○ | ○ | ○ | ○ | ○ | ○ | ○ | ○ |
| | | 05/01/2015 05:55 | ✓ | E | 275 | 127 | Clean catch | ○ | ○ | ○ | ○ | ○ | ○ | ○ | ○ | ○ | ○ |
| | | 05/03/2015 09:12 | ✓ | F | 145 | 128 | Indwelling UC | ○ | ○ | ○ | ○ | ○ | ○ | ○ | ○ | ○ | ○ |
| ③ Variant call | Running 0<br>Passed 15<br>Warning 0<br>Failed 0 | 05/02/2015 12:20 | ✓ | G | 893 | 129 | Clean catch | ○ | ○ | ○ | ○ | ○ | ○ | ○ | ○ | ○ | ○ |
| | | 04/29/2015 23:44 | ✓ | H | 347 | 130 | BLOOD | ○ | ○ | ○ | ○ | ○ | ○ | ○ | ○ | ○ | ○ |
| ④ MLST | Running 0<br>Passed 14<br>Warning 0<br>Failed 1 | 04/28/2015 16:24 | ✓ | I | 736 | 131 | Clean catch | ○ | ○ | ○ | ○ | ○ | ○ | ○ | ○ | ○ | ○ |
| | | 04/30/2015 12:23 | ✓ | J | 085 | 132 | Clean catch | ○ | ○ | ○ | ○ | ○ | ○ | ○ | ○ | ○ | ○ |
| | | 05/01/2015 05:30 | ✓ | K | 458 | 133 | PERITONEAL | ○ | ○ | ○ | ○ | ○ | ○ | ○ | ○ | ○ | ○ |
| ⑤ Phylogeny tree | Running 0<br>Passed 14<br>Warning 0<br>Failed 0 | 05/01/2015 03:18 | ✓ | L | 276 | 134 | Sputum | ○ | ○ | ○ | ○ | ○ | ○ | ○ | ○ | ○ | ○ |
| | | 05/03/2015 05:55 | ✓ | M | 237 | 135 | Sputum | ○ | ○ | ○ | ○ | ○ | ○ | ○ | ○ | ○ | ○ |
| | | 05/03/2015 09:12 | ✓ | N | 111 | 136 | PERITONEAL | ○ | ○ | ○ | ○ | ○ | ○ | ○ | ○ | ○ | ○ |
| | | 05/02/2015 12:20 | ✓ | O | 170 | 137 | BLOOD | ○ | ○ | ○ | ○ | ○ | ○ | ○ | ○ | ○ | ○ |
| ⑥ Summary | Running 0<br>Passed 14<br>Warning 2<br>Failed 4 | 04/28/2015 23:44 | ✓ | P | 076 | 138 | Clean catch | ○ | ○ | ○ | ○ | ○ | ○ | ○ | ○ | ○ | ○ |

| Name | Accession # | Basic stat. | Per base seq. qual. | Per base seq. qual. score | Per base seq. cont. | Per seq. GC cont. | Per base GC cont. | Per base N cont. | Seq. len. dis. | Seq. dup. lvl. | Overrepresented seq. | Kmer cont. | bamQC | Unfiltered variant calls | Variant calls | base calls | Normalized base calls |
|---|---|---|---|---|---|---|---|---|---|---|---|---|---|---|---|---|---|
| A | 123 | ○ | ○ | ○ | ○ | ○ | ○ | ○ | ○ | ○ | ○ | ○ | 67 | 4361 | 3835 | 2427385 | 0.8091 |
| B | 124 | ○ | ○ | ○ | ○ | ○ | ○ | ○ | ○ | ○ | ○ | ○ | 89 | 6398 | 4187 | 2480726 | 0.8269 |
| C | 125 | ● | ○ | ● | ○ | ○ | ○ | ○ | ● | ○ | ○ | ○ | 75 | 5343 | 6142 | 2510602 | 0.8369 |
| D | 126 | ○ | ○ | ○ | ○ | ○ | ○ | ○ | ○ | ○ | ○ | ○ | 88 | 6124 | 5129 | 2569148 | 0.8564 |
| E | 127 | ○ | ○ | ○ | ○ | ○ | ○ | ○ | ○ | ○ | ○ | ○ | 76 | 4314 | 5879 | 2472158 | 0.8241 |
| F | 128 | ○ | ○ | ○ | ○ | ○ | ○ | ○ | ○ | ○ | ○ | ○ | 82 | 6257 | 4141 | 2479850 | 0.8266 |
| G | 129 | ○ | ○ | ○ | ○ | ○ | ○ | ○ | ○ | ○ | ○ | ○ | 69 | 6301 | 6007 | 2548367 | 0.8495 |
| H | 130 | ○ | ○ | ○ | ○ | ○ | ○ | ○ | ○ | ○ | ○ | ○ | 65 | 6463 | 6049 | 2547973 | 0.8493 |
| I | 131 | ○ | ○ | ○ | ○ | ○ | ○ | ○ | ○ | ○ | ○ | ○ | 70 | 4398 | 6204 | 2502690 | 0.8342 |
| J | 132 | ○ | ○ | ○ | ○ | ○ | ○ | ○ | ○ | ○ | ○ | ○ | 79 | 7439 | 4222 | 2526437 | 0.8421 |
| K | 133 | ○ | ○ | ○ | ○ | ○ | ○ | ○ | ○ | ○ | ○ | ○ | 88 | 6230 | 7141 | 2595564 | 0.8652 |
| L | 134 | ○ | ○ | ○ | ○ | ○ | ○ | ○ | ○ | ○ | ○ | ○ | 81 | 4502 | 5981 | 2555705 | 0.8519 |
| M | 135 | ○ | ○ | ○ | ○ | ○ | ○ | ○ | ○ | ○ | ○ | ○ | 71 | 4452 | 4322 | 2496189 | 0.8321 |

|   |   |   |   |   |   |   | ED8 | ED7 | ED6 | ED5 |
|---|---|---|---|---|---|---|---|---|---|---|
|   | MRI1 | MRI2 |   | XRAY3 | XRAY2 | XRAY1 |   |   |   |   |
|   | 1Proc3 | 1Proc4 |   |   |   |   |   |   |   | ED4 |
|   |   |   |   | ELE3 |   |   |   | ELE4 |   |   |
|   | 1Proc2 | ELE1 |   |   |   |   |   |   |   | ED3 |
|   | 1Proc1 | ELE2 |   | Lab |   |   |   |   |   |   |
|   |   |   |   |   |   |   |   |   |   | ED2 |
| 1 | CT1 | CT2 |   |   | Main ent. |   |   |   |   | ED1 |
|   |   |   |   |   |   |   | ICU8 | ICU7 | ICU6 | ICU5 |
|   | OR6 | OR5 | OR4 | OR3 | OR2 | OR1 |   |   |   |   |
|   |   |   |   |   |   |   |   |   |   | ICU4 |
|   |   |   |   | ELE3 |   |   |   | ELE4 |   |   |
|   |   | ELE1 |   |   |   |   |   |   |   | ICU3 |
|   |   | ELE2 | SICU8 | SICU6 | SICU4 | SICU2 |   |   |   |   |
|   |   |   |   |   |   |   |   |   |   | ICU2 |
|   | SICU10 | SICU9 | SICU7 | SICU5 | SICU3 | SICU1 |   |   |   |   |
| 2 |   |   |   |   |   |   |   |   |   | ICU1 |
|   | Grow9 | Grow5 | Grow6 |   | Grow1 | Grow2 |   |   |   |   |
|   | Grow10 | Grow8 | Grow7 |   | Grow4 | Grow3 | NICU1 | NICU2 | NICU3 | NICU4 |
|   | Grow11 |   |   |   |   |   |   |   |   |   |
|   | Grow12 |   |   |   |   |   |   |   |   | NICU5 |
|   |   |   |   | ELE3 |   |   |   | ELE4 |   |   |
|   |   | ELE1 |   |   |   |   |   | 3Proc1 |   |   |
|   |   | ELE2 | PICU8 | PICU6 | PICU4 | PICU2 |   | 3Proc2 |   |   |
|   |   |   |   |   |   |   |   | 3Proc3 |   | NICU7 |
|   | PICU10 | PICU9 | PICU7 | PICU5 | PICU3 | PICU1 |   | 3Proc4 |   |   |
| 3 |   |   |   |   |   |   |   |   |   | NICU8 |

FIG. 6a

| Label | Xcoordinate | Ycoordinate | Zcoordinate |
|---|---|---|---|
| ED1 | 5 | 1 | 1 |
| ED2 | 5 | 3 | 1 |
| ED3 | 5 | 5 | 1 |
| ED4 | 5 | 7 | 1 |
| ED5 | 5 | 9 | 1 |
| ED6 | 4 | 9 | 1 |
| ED7 | 3 | 9 | 1 |
| ED8 | 2 | 9 | 1 |
| XRAY1 | 1 | 7 | 1 |
| XRAY2 | 0 | 7 | 1 |
| XRAY3 | -1 | 7 | 1 |
| MRI1 | -4 | 7 | 1 |
| MRI2 | -3 | 7 | 1 |
| 1PROC1 | -4 | 3 | 1 |
| 1PROC2 | -4 | 4 | 1 |
| 1PROC3 | -4 | 6 | 1 |

FIG. 6b

Not utilizing directions
phylo tree - SNP data

Not utilizing phylo tree at all

Utilizing phylo tree
directions - SNP data

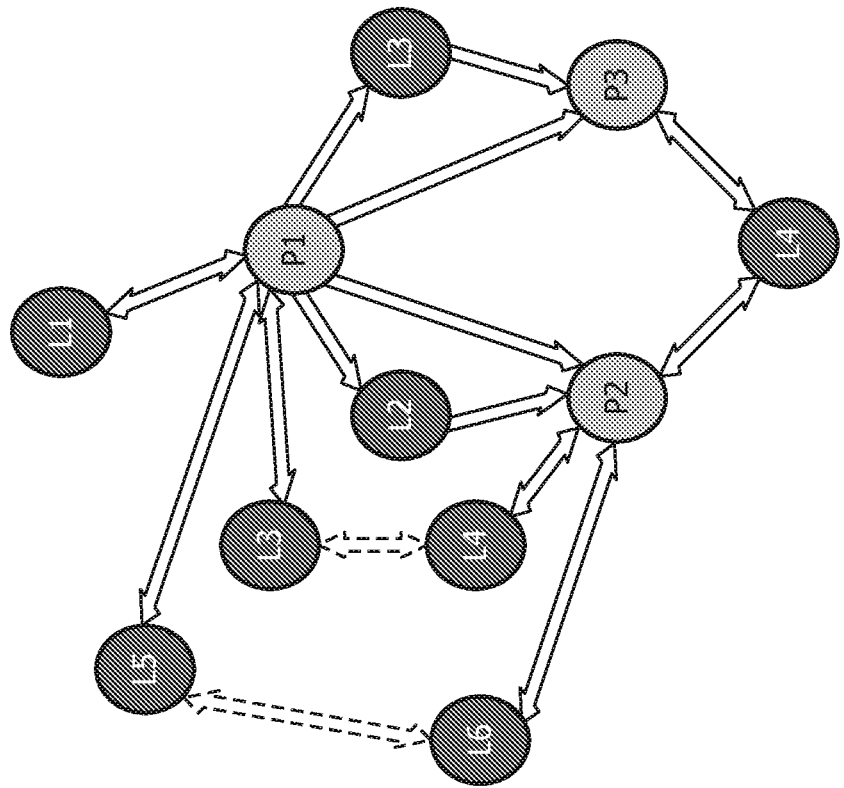
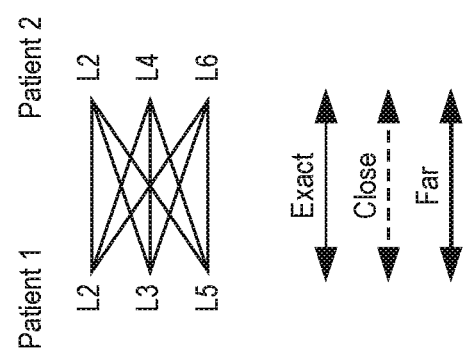
FIG. 10

• Weighting edges based on pairwise SNP difference values

Output of C# implementation

Reading input network file to build the graph ... done.
    ... took 3.2695 milliseconds for 14 nodes and 42 edges.
Running power iteration on data set ... done.
    ... took 0.7057 milliseconds for 22 iterations.

| node# | rank | rank% |
|---|---|---|
| cA | 2.18752625383162 | 31.2445291388898 |
| cE | 1.27471410339193 | 18.2067949481391 |
| cG | 1.17377317782505 | 16.7650514789318 |
| cF | 0.751976552147067 | 10.7405126014682 |
| cB | 0.624101533475376 | 8.91406835193037 |
| cC | 0.49460904688366 | 7.06452174032038 |
| cD | 0.49460904688366 | 7.06452174032038 |

| location1 | location2 | distance |
|---|---|---|
| L1 | L2 | 3 |
| L1 | L3 | 1 |
| L1 | L4 | 8 |
| L1 | L5 | 4 |
| L1 | L6 | 3 |
| L1 | L7 | 7 |
| L2 | L3 | 11 |
| L2 | L4 | 6 |
| L2 | L5 | 8 |
| L2 | L6 | 12 |
| L2 | L7 | 2 |
| L3 | L4 | 14 |
| L3 | L5 | 9 |
| L3 | L6 | 4 |
| L3 | L7 | 2 |
| L4 | L5 | 5 |
| L4 | L6 | 10 |
| L4 | L7 | 13 |
| L5 | L6 | 6 |
| L5 | L7 | 8 |
| L6 | L7 | 8 |

FIG. 14c

| patient1 | patient2 | SNP_diference |
|---|---|---|
| pX | pY | 1 |
| pX | pU | 2 |
| pX | pS | 2 |
| pX | pZ | 5 |
| pX | pV | 6 |
| pX | pW | 5 |
| pY | pU | 8 |
| pY | pS | 14 |
| pY | pZ | 1 |
| pY | pV | 15 |
| pY | pW | 16 |
| pU | pS | 18 |
| pU | pZ | 19 |
| pU | pV | 1 |
| pU | pW | 1 |
| pS | pZ | 12 |
| pS | pV | 14 |
| pS | pW | 16 |
| pZ | pV | 21 |
| pZ | pW | 18 |
| pV | pW | 8 |

No edge weighting

| node# | rank | rank% |
|---|---|---|
| L1 | 1.742 | 17.278 |
| L7 | 1.686 | 16.719 |
| L5 | 1.582 | 15.689 |
| L6 | 1.282 | 12.717 |
| L2 | 1.264 | 12.536 |
| L4 | 1.264 | 12.531 |
| L3 | 1.264 | 12.531 |

FIG. 15a

Edge weighting using SNPs difference

| node# | rank | rank% |
|---|---|---|
| L1 | 2.034 | 20.225 |
| L5 | 1.603 | 15.937 |
| L7 | 1.577 | 15.682 |
| L6 | 1.272 | 12.651 |
| L2 | 1.218 | 12.107 |
| L3 | 1.177 | 11.700 |
| L4 | 1.177 | 11.699 |

FIG. 15b

Edge weighting using locations distance

| node# | rank | rank% |
|---|---|---|
| L1 | 1.925 | 21.180 |
| L7 | 1.470 | 16.171 |
| L3 | 1.402 | 15.425 |
| L5 | 1.314 | 14.456 |
| L2 | 1.129 | 12.418 |
| L6 | 0.961 | 10.568 |
| L4 | 0.889 | 9.782 |

FIG. 15c

Edge weighting using SNPs difference AND locations distance

| node# | rank | rank% |
|---|---|---|
| L1 | 2.315 | 25.465 |
| L5 | 1.349 | 14.840 |
| L7 | 1.323 | 14.555 |
| L3 | 1.320 | 14.518 |
| L2 | 1.058 | 11.637 |
| L6 | 0.963 | 10.597 |
| L4 | 0.762 | 8.389 |

FIG. 15d

METHODS, SYSTEMS AND PROCESSES OF DETERMINING TRANSMISSION PATH OF INFECTIOUS AGENTS

CROSS-REFERENCE TO PRIOR APPLICATIONS

This application is the U.S. National Phase application under 35 U.S.C. § 371 of International Application No. PCT/IB2016/056497, filed on Oct. 28, 2016, which claims the benefit of U.S. Provisional Application Ser. No. 62/248,555, filed Oct. 30, 2015. These applications are hereby incorporated by reference herein, for all purposes.

RELATED PATENT APPLICATIONS

This patent application claims the benefit of U.S. Provisional Patent Application No. 62/248,555 filed on Oct. 30, 2015, entitled A System And Method To Determine Transmission Paths For Genetically Related Infections, naming Brian Gross, Thomas Chou, Saeed Babaeizadeh, Autri Dutta, Henry Lin and Andrew Arthur as inventors. The entire content of the foregoing application is incorporated herein by reference, including all text, tables and drawings.

FIELD

This technology relates in part to computer-implemented methods, processes and systems of generating a transmission metric to determine and/or track transmission of a pathogen.

BACKGROUND

One challenge in the use of next-generation sequencing (NGS) techniques in pathogen identification and infection control is that while genetically related and unrelated infections can be identified and distinguished, the transmission pathways require a tedious review of each patient trajectory through the care system to match possible pathogens and patient trajectories.

SUMMARY

As presented herein, certain embodiments of this invention facilitates sequence matching to microbiology results from where an isolate for a sequence was cultured, overviewing the sequence upload to a genomics sequence processing system, executing and monitoring the processing, and assignment of surveillance, caregiver and environmental cultures to sequences results. In certain embodiments, this invention also provides time navigation tools by way of an epidemiology curve (Epi Curve), pathogen selection, and rendering of a resulting phylogeny tree. In some embodiments presented herein, nodes on the pathogen specific phylogenetic trees are linked to clinical correlate data obtained for the patient, including but not limited to caregivers, equipment, location history, and environmental interactions by the patient with one or more pathogen sources. In some embodiments presented herein, selecting a patient sample can provide disclosure of the sample details including access to the sequence pipeline QC results for each step of the mission, as well as likely clinical transmission vectors based on analysis of the genetic relatedness of infections and collected correlate data.

In certain embodiments herein, decorations on a phylogeny tree indicate where there is a direct match to a common clinical correlate, as well as the most likely correlates based on a probability calculation that is linked to the genetic similarity of the pathogens. In representing potential transmissions, a transmission metric can be determined according to patient samples and/or clinical correlates, in certain embodiments presented herein.

In some aspects provided herein is a computer-implemented method for determining a transmission metric for related pathogens comprising: a) providing a plurality of proximity tags for each of a plurality of objects, wherein each proximity tag comprises (i) a unique object identifier associated with an object, and (ii) a probable coordinate defining a location of the object within a period of time; b) providing a plurality of pathogen tags, wherein each pathogen tag comprises a proximity tag, a unique pathogen identifier, and genomic sequence data obtained from a pathogen; c) identifying a set of related pathogens according to a relationship between the plurality of pathogen tags, thereby providing a set of related pathogen tags; d) determining the presence of one or more relationships between one or more of the plurality of proximity tags and one or more of the set of related pathogen tags according to probabilistic correlations, thereby providing a transmission metric comprising a subset of related proximity tags. In certain embodiments, the transmission metric comprises interactive nodes and edges presented on a display, each node comprising a pathogen tag or a proximity tag, and each edge comprising a probability of transmission. In certain embodiments the relationship between the plurality of pathogen tags comprises a relationship between the genomic sequence data and a relationship between the proximity tags. In certain embodiments the genomic sequence data comprises one or more genetic variations associated with a pathogen. In certain embodiments the genomic sequence data comprises one or more genetic variations associated with a pathogen. In certain embodiments related pathogens of the set are identified according to a correlation between the one or more genetic variations and the period of time of a proximity tag. In some embodiments related pathogens of the set are identified according to a correlation between the one or more genetic variations and the probable coordinate of the object. In some aspects related pathogens of the set are identified according to a correlation between the one or more genetic variations and an expected mutation rate.

An object can be a device or a subject (e.g., a human subject, a patient, a medical practitioner). Where a human subject is a patient, the proximity tag associated with the patient often comprises clinical information related to the patient. In certain embodiments a probable coordinate is a three-dimensional coordinate. In certain embodiments related pathogens are identified by a process comprising a Random Walk or weighted Markov Chains. In certain embodiments the probabilistic correlations comprise probabilistic matches between of the probable coordinates of two or more proximity tags and the probable coordinates of one or more of the related pathogen tags. In certain embodiments determining the presence of one or more relationships in (d) comprises determining one or more temporal relationships between one or more human subjects and one or more related pathogens. In certain embodiments the temporal relationships comprise one or more probable intersects between two or more proximity tags. In certain embodiments a coordinate is within one or more defined regions which comprise one or more hospitals. In certain embodiments identifying a set of related pathogens comprises identifying one or more of the set of related pathogens to a sub-species level or strain level according to the genomic sequence data. In some embodiments identifying the set of related pathogens comprises MLST typing, identification of gene expression signatures, determining a pathogen's closest neighbor, determining a pathogen's mutation rate, determining pathogen growth rates, determining a pathogen's evolutionary distance between two or more other pathogens and/or generating a phylogenetic metric or phylogenetic tree. In certain embodiments a pathogen is a species of ESAKPE pathogen. In certain embodiments a transmission path of related pathogens is determined according to the transmission metric. In certain embodiments a parent pathogen or a patient zero is identified according to a transmission path. In some embodiments a probable location of a related pathogen is predicted according to the transmission path.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 2 shows an embodiment of a display output showing sequence status overview.

FIG. 3 shows an embodiment of a display output showing sequence analysis status summary.

FIG. 4 shows an embodiment of a display output showing a sequence summary overview with collapsed status steps and "BamQC" accordion closed review.

FIG. 6a shows a floor plan and FIG. 6b shows coordinates (in room units) from common reference points (e.g., main entrance) within a defined area.

FIG. 10 shows an embodiment of a transmission metric of a subset of related proximity tags represented by nodes (circles) and edges (arrows). Nodes P1, L3 and L5 represent proximity tags associate with patient 1, wherein the proximity tags share a common unique object identifier. Nodes P2, L4 and L6 represent proximity tags associate with patient 2, wherein the proximity tags share a common unique object identifier. Node L1 can represent a proximity tag for a device or a subject number 3. In some embodiments L2 represent an intersect of two proximity tags, one associated with patient 1 and another associated with patient 2. L2 can be represented by a single node (i.e., an exact intersect) or by two separate nodes (e.g., a proximity tag for each patient and an edge indicating an exact intersect or match). Where P1 and P2 comprise a pathogen tag, and the pathogen is determined from genomic sequence data to be related, directional transmission can often be determined.

FIGS. 11A and 11B show an embodiment of a transmission metric for a subset of pathogens determined to be highly related strains where the enclosed circles represent patient nodes indicated by p (e.g., pS, pU, pV pW, pX, pY, and pZ) and caregivers nodes indicated by c (e.g., cA, cB, cC, cD, cE, cF and cG). In this example, edges (small arrows) are shown only between patients and caregivers. Wide arrows represent a relationship between pathogens (pathogen tags or a phylogeny tree). In this example, for simplicity, it is assumed a patient to patient contact is highly unlikely or did not occur. In certain embodiments, edges between a patient and caregiver are weighted and/or normalized, where the sum of all outgoing weights for a node is 1 (for example see weighted edges in FIG. 11B from caregiver cA to patients pX, pU, pV, pZ and pY). In the example of FIG. 11B a uniform outgoing weighting for each caregiver node is provided where the caregiver is equally likely to receive a pathogen from any patient (pX, pU, pV, pZ and pY) that the caregiver came into contact with.

FIG. 13B shows a rank determined for each caregiver node as determined by a modification of PageRank (e.g., retrieved from the Internet) Each rank was determined according to the normalized weighted values shown in FIG. 13A using a modified PageRank algorithm. FIG. 13B also shows normalized rank values (Percent Rank) for each caregiver node where the sum of the rank % for each caregiver node equals 100.

FIG. 14B shows a table listing distances determined between each set of location nodes. Distances can be expressed in any suitable manner (e.g., 2 dimensional coordinates, Cartesian coordinates (i.e., 3 dimensional coordinates), an array of locations in Euclidian space). FIG. 14C shows a table listing SNP difference between pathogens for each pair of patient nodes.

FIG. 15 shows a comparison between node ranks for nodes L1-L7 determined with no edge weighting (FIG. 15A), edge weighting using SNP differences (FIG. 15B), edge weighting using location distances (FIG. 15C) and edge weighting using a combination of edge weighting using SNP differences and location distances (FIG. 15D).

DETAILED DESCRIPTION

Figure 1:
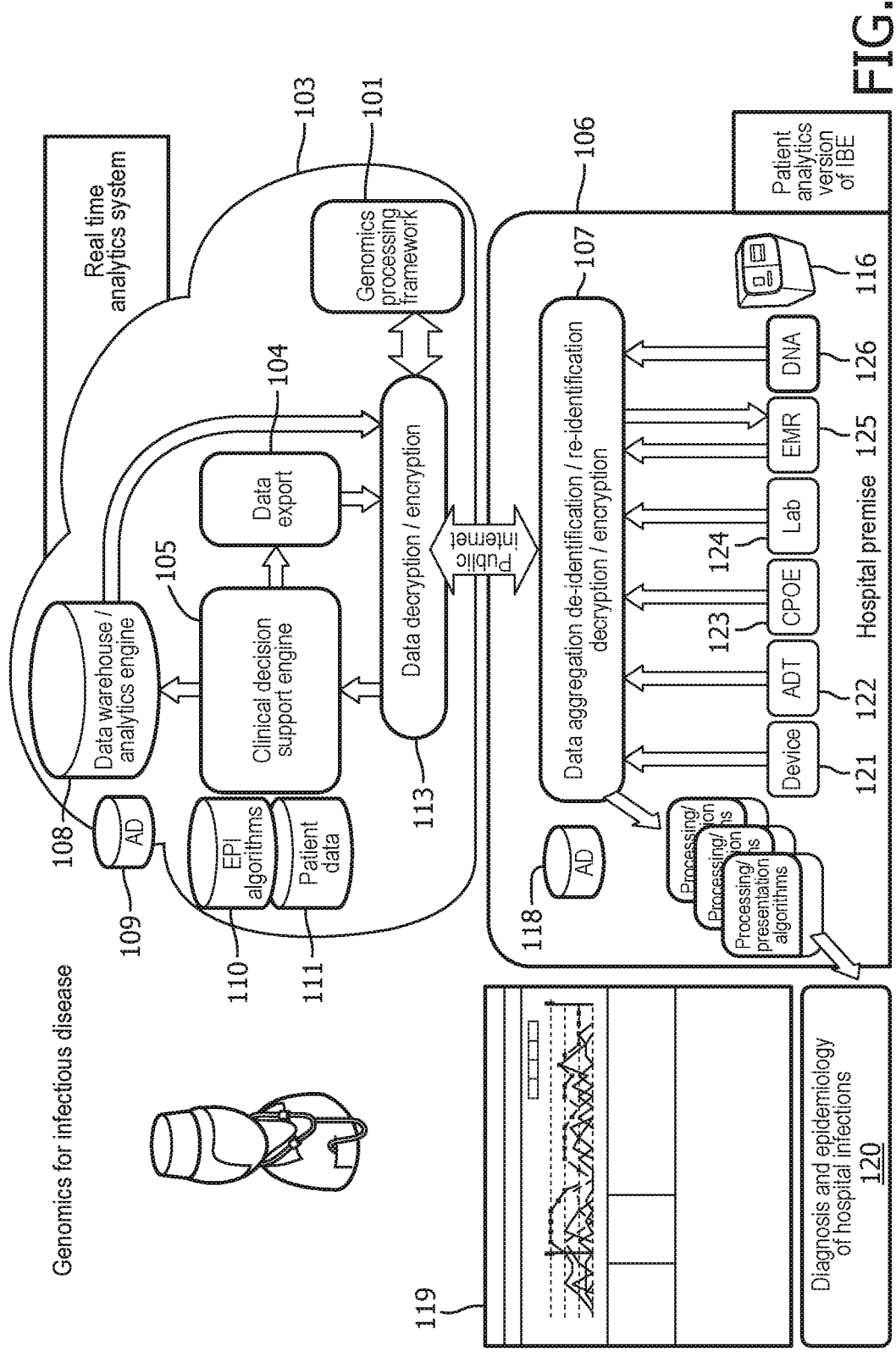
FIG. 1 shows an embodiment of a system hosted on a networked computing platform which includes a plurality of complementary analytics systems including a genomics pipeline processing system (GPPS) 101 and a real time patient analytics system 103.
Figure 5:
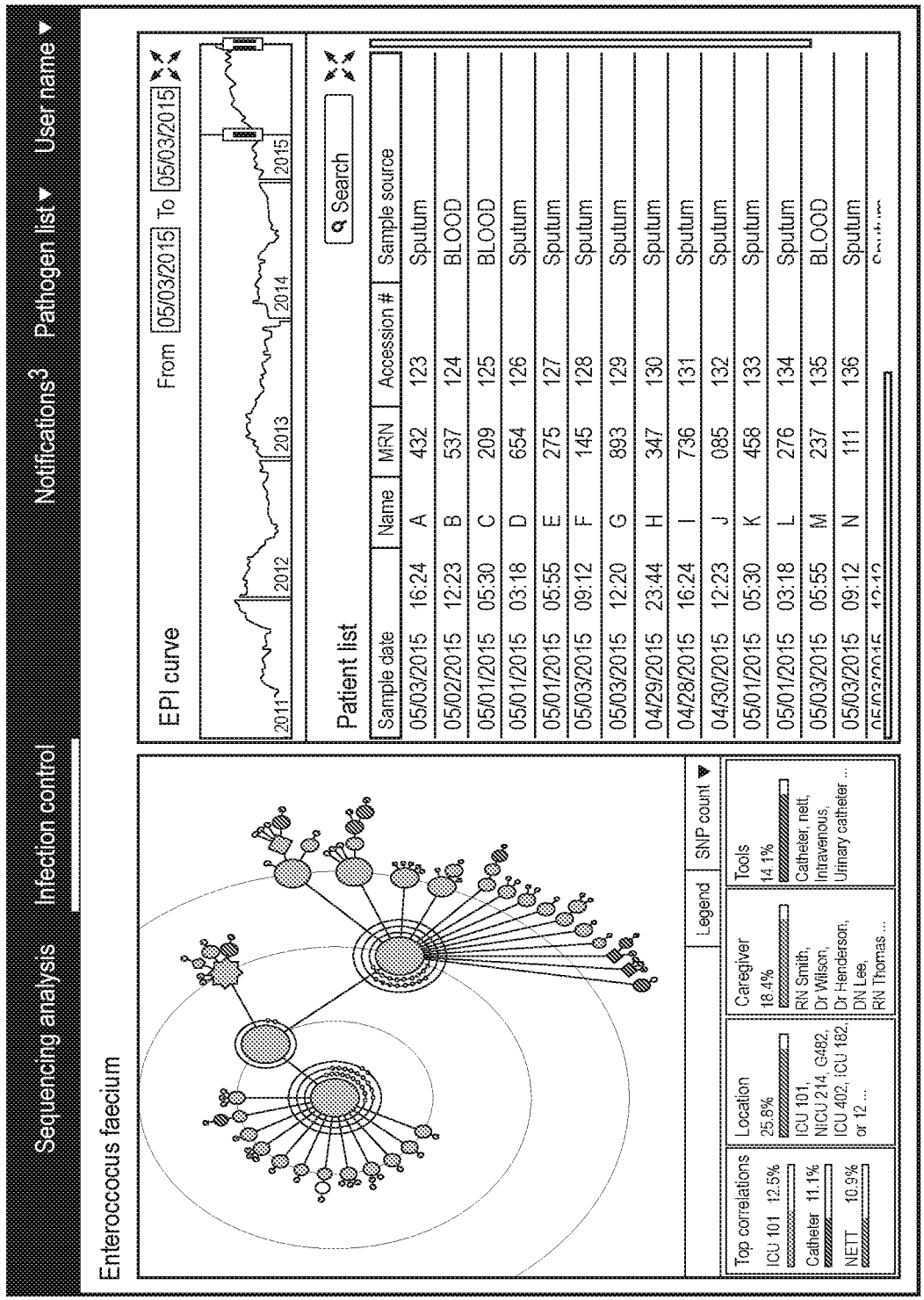
FIG. 5 shows a phylogeny tree with associated epi curve navigator and relevant patient data.

Provided herein are computer-implemented methods to analyze and track transmission of a pathogen by generating a transmission metric utilizing genomic sequence data obtained from samples comprising nucleic acids of related pathogens, as well as time and coordinate information associated with a subject and/or an object. The use of the generated transmission metric may, for example, enable a computer system to analyze and track pathogen transmissions significantly faster, as compared to conventional computer-assisted analysis and tracking of pathogen transmissions. In some embodiments, the resulting transmission metric comprises a graph having nodes and edges where each node represents objects (e.g., infected patients, caregivers, contaminated devices) and edges representing probable transmission paths of a pathogen between nodes. The generation of such a graph (usable for analysis and tracking of pathogen transmission) as described herein may provide significant improvements to traditional approaches of generating transmission path graphs. As an example, such improvements may result from the edges of the transmission metric being weighted by a novel weighting algorithm that incorporates variables such as genetic similarities or differences between pathogens, location parameters and/or time. Each node is then ranked according to the weighting of each edge that contacts a node, and ranking values can be used to identify probable pathogen vectors and track the probable origins and paths of a pathogen for a given outbreak. The computer-implemented methods presented herein can generate a novel transmission metric and rank nodes significantly faster than traditional approaches that produce inferior transmission graphs.

Information associated with a subject and/or an object is often referred to herein as a proximity tag. Information related to a pathogen is often referred to herein as a pathogen tag. In some embodiments, a proximity tag comprises a pathogen tag. In some embodiments, related pathogens are identified according to a plurality of pathogen tags, and the genomic sequence data contained therein. In certain embodiments, decorations or nodes on a phylogeny tree indicate where there is a direct match between common clinical correlates, as well as the most likely correlates based on a probability calculation that is linked to the genetic similarity of the infections. In certain embodiments, transmission metrics provided herein are generated, in part, using information of proximity tags and pathogen tags, and using probabilistic methods to provide probable intersects of certain tags and to provide probable transmission paths of related pathogens.

Objects & Subjects

An object can be any physical or material thing that can be seen, detected or touched. Non-limiting examples of an object include a device (e.g., a bronchoscope with serial number xyz), furniture, chair, computer, table, a floor, a wall, a window, a door, a vent, an air filter (e.g., an intake or vent filter), air (e.g., an air sample), a liquid, a subject, a plant, a vehicle, the like, any part thereof or combinations thereof. An object can be stationary or mobile. In some embodiments, an object is a subject (e.g., a human subject).

A subject can be any animal, living or non-living, including but not limited to a mammal, a human, a non-human animal, a fish, a bird, a farm animal, and the like. A subject may be any age (e.g., an embryo, a fetus, infant, child, adult). A subject can be of any sex (e.g., male, female, or combination thereof). In some embodiments, a subject is a mammal. In some embodiments, a subject is a human subject. A subject can be a patient (e.g., a human patient). In some embodiments, a subject is infected with a pathogen (e.g., a related pathogen). In certain embodiments, a subject is a person present in a medical care facility or a person employed by a medical care facility. In certain embodiments, a subject is a medical professional or a caregiver.

Defined Regions

In certain embodiments, an object is located within a defined region. In some embodiments, a defined region is one or more defined areas. A location, area or region can be defined by one or more two-dimensional and/or three-dimensional coordinates. A location can be an exact location or a probable location. Non-limiting examples of a defined region include a country, a city, a city block, a portion of land, a building, a hospital, a park, a vehicle, a building complex, or combinations thereof. In certain embodiments, a defined region includes any region or area that can be monitored by a process or system described herein or known in the art. For example, a defined region can be any collection of regions wherein proximity tags and/or pathogens tags of the instant invention can be located, tracked and/or monitored. For example, in certain embodiments, a defined region includes a collection of hospitals (e.g., 2, 3, 4, 5, 6 or 10 or more hospitals), medical facilities, rooms and medical transport vehicles that can be networked, tracked and/or monitored. In one embodiment, a defined area may include a path traveled by an object, wherein a system herein can determine an exact or probable location (e.g., coordinate) of an object for an exact or probable period of time.

In certain embodiments, a defined region is any region where a pathogen reservoir may exist. For example, a defined region may include a skilled nursing facility, a nursing home or an outbreak treatment zone, and the like.

In certain embodiments, samples are obtained, isolated and/or analyzing. A sample (e.g., a sample comprising nucleic acid) can be obtained from a suitable object. A sample can be any specimen that is isolated or obtained from an object, or part thereof. A sample can be any specimen that is isolated or obtained from a subject. A sample can be obtained directly or indirectly from an object, or part thereof. In some embodiments, a sample is provided by individual or medical professional who isolated a sample directly from an object. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid). A sample may be obtained from living or non-living object. For example, a sample may be a swap or isolate obtained from a device, a room (e.g., a door, a wall, an air sample), a table, chair, clothing, etc. A sample can be obtained using any suitable method.

In some embodiments, a sample comprises nucleic acid, or fragments thereof. A sample can comprise nucleic acids obtained from one or more subjects. In some embodiments a sample comprises nucleic acid derived from a pathogen (e.g., a virus, bacteria, fungus, and the like). A pathogen can be any microorganism or parasite that can infect or reside in a mammalian host, non-limiting examples of which include a virus, a bacteria, a fungus, a parasite, a prion, and the like. In certain embodiments, a sample comprises an entire genome of an organism. In some embodiments, a sample comprises a portion of a genome of an organism. In some embodiments, a sample comprises a mixture of nucleic acids (e.g., nucleic acids derived from two or more organisms). A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. A sample may comprise synthetic nucleic acid.

Nucleic acid may be derived, isolated, extracted, purified or partially purified from one or more sources, or one or more samples using suitable methods known in the art. Any suitable method can be used for isolating, extracting and/or purifying nucleic acid.

The terms "nucleic acid" refers to one or more nucleic acids (e.g., a set or subset of nucleic acids) of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. In some embodiments nucleic acid refers to genomic DNA. Unless specifically limited, the term encompasses nucleic acids comprising deoxyribonucleotides, ribonucleotides and known analogs of natural nucleotides. A nucleic acid may include, as equivalents, derivatives, or variants thereof, suitable analogs of RNA or DNA synthesized from nucleotide analogs, single-stranded ("sense" or "antisense", "plus" strand or "minus" strand, "forward" reading frame or "reverse" reading frame) and double-stranded polynucleotides. Nucleic acids may be single or double stranded. A nucleic acid can be of any length of 2 or more, 3 or more, 4 or more or 5 or more contiguous nucleotides. A nucleic acid can comprise a specific 5' to 3' order of nucleotides known in the art as a sequence (e.g., a nucleic acid sequence, e.g., a sequence).

A nucleic acid may be naturally occurring and/or may be synthesized, copied or altered (e.g., by a technician, scientist or one of skill in the art). For, example, a nucleic acid may be an amplicon. A nucleic acid may be from a nucleic acid library, such as a gDNA, cDNA or RNA library, for example. A nucleic acid can be synthesized (e.g., chemically synthesized) or generated (e.g., by polymerase extension in vitro, e.g., by amplification, e.g., by PCR). A nucleic acid may be, or may be from, a plasmid, phage, virus, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. Nucleic acids (e.g., a library of nucleic acids) may comprise nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic Acid Sequencing

In certain embodiments nucleic acids are analyzed by a process comprising nucleic acid sequencing. In some embodiments, nucleic acids may be sequenced. In some embodiments, a full or substantially full sequences are obtained and sometimes a partial sequence is obtained.

A suitable method of sequencing nucleic acids can be used, non-limiting examples of which include Maxim & Gilbert, Sanger, chain-termination methods, sequencing by synthesis, sequencing by ligation, sequencing by mass spectrometry, microscopy-based techniques, the like or combinations thereof. In some embodiments, a high-throughput sequencing method is used. High-throughput sequencing methods generally involve clonally amplified DNA templates or single DNA molecules that are sequenced in a massively parallel fashion, sometimes within a flow cell.

Next generation (e.g., 2nd and 3rd generation, etc.) sequencing (NGS) techniques are capable of sequencing DNA in a massively parallel fashion and can be used for methods described herein. NGS and "massively parallel sequencing" (MPS) methods are collectively referred to herein as MPS. Any suitable MPS or next generation sequencing method, system or technology platform for conducting methods described herein can be used to obtain sequencing reads, non-limiting examples of which include Illumina/Solex/HiSeq (e.g., Illumina's Genome Analyzer; Genome Analyzer II; HISEQ 2000; HISEQ 2500, SOLiD, Roche/454, PACBIO, SMRT, Helicos True Single Molecule Sequencing, Ion Torrent and Ion semiconductor-based sequencing, WildFire, 5500, 5500xl W and/or 5500xl W Genetic Analyzer based technologies (e.g., as developed and sold by Life Technologies), nanopore sequencing (e.g., Oxford Nanopore Technologies), Polony sequencing; Pyrosequencing, Massively Parallel Signature Sequencing, RNA polymerase (RNAP) sequencing, IBS methods, LaserGen systems and methods, chemical-sensitive field effect transistor (CHEMFET) array, electron microscopy-based sequencing, nanoball sequencing, sequencing-by-synthesis, sequencing by ligation, sequencing-by-hybridization, the like or variations thereof. Additional sequencing technologies that include the use of developing nucleic acid imaging technologies (e.g., transmission electron microscopy (TEM) and atomic force microscopy (AFM)), also are contemplated herein. In some embodiments, a high-throughput sequencing method is used. High-throughput sequencing methods generally involve clonally amplified DNA templates or single DNA molecules that are sequenced in a massively parallel fashion, sometimes within a flow cell. In some embodiments MPS sequencing methods utilize a targeted approach, where sequence reads are generated from specific chromosomes, genes or regions of interest. Specific chromosomes, genes or regions of interest are sometimes referred to herein as targeted genomic regions. In certain embodiments a non-targeted approach is used where most or all nucleic acid fragments in a sample are sequenced, amplified and/or captured randomly. In certain embodiments sequence reads are obtained by a method comprising paired-end sequencing. In certain embodiments, a first generation technology, such as, for example, Sanger sequencing methods including automated Sanger sequencing methods, including microfluidic Sanger sequencing, can be used in a method provided herein for the purpose of confirming whether a variation detected to be in either of the gene of interest or the counterpart is in fact in the gene of interest.

Subjecting a nucleic acid to a sequencing method (e.g., an NGS sequencing method) often provides sequence reads. In certain embodiments, sequence reads are obtained for an entire genome or for a portion of a genome of one or more organisms (e.g., a subject or pathogen). Sequence reads can be obtained by any suitable nucleic acid sequencing method. In certain embodiments, sequence reads are obtained by an MPS method. As used herein, "reads" (e.g., "a read", "a sequence read") are short nucleotide sequences produced by any sequencing process described herein or known in the art. Reads can be generated from one end of a nucleic acid fragment ("single-end reads"), and sometimes are generated from both ends of a nucleic acid fragment (e.g., paired-end reads, paired-end sequence reads, double-end reads). Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. A mixture of relatively short reads can be transformed by processes described herein into a representation of a genome (e.g., genomic nucleic acid) present in subject or pathogen. Reads of a mixture of nucleic acids from one or more subjects can be transformed into a representation of a genome, or portion thereof, for each of the subjects or pathogens.

In certain embodiments, "obtaining" nucleic acid sequence reads of a sample from a subject and/or "obtaining" nucleic acid sequence reads of a biological specimen (e.g., a sample) obtained from one or more subjects can involve directly sequencing nucleic acid to obtain the sequence information. In some embodiments, "obtaining" can involve receiving sequence information obtained directly from a nucleic acid by another. For example, in some embodiments, sequence information (e.g., sequencing reads) are provided or obtained in the form of an electronic file (e.g., a non-transitory computer-readable media).

NGS sequence methods often comprise mapping sequence reads. In some embodiments, sequence reads are mapped. In some embodiments a suitable mapping method, process or algorithm is used. In certain embodiments modified mapping methods and processes are used herein. Mapping nucleotide sequence reads (e.g., sequence information from a fragment whose physical genomic position is unknown) can be performed in a number of ways, and often comprises alignment of the obtained sequence reads, or portions thereof, with a matching sequence in a reference genome. In such alignments, sequence reads generally are aligned to a reference sequence and those that align are designated as being "mapped", "a mapped sequence read" or "a mapped read".

As used herein, the terms "aligned", "alignment", or "aligning" refer to two or more nucleic acid sequences that can be identified as a match (e.g., 100% identity) or partial match. Methods of aligning nucleic acid sequences are known and any suitable alignment method can be used for a method, system, process, module or program described herein. Alignments can be performed manually (e.g., for small projects) or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match (e.g., 100% identity). In some cases, an alignment is less than a 100% identity (e.g., non-perfect match, partial match, partial alignment). In some embodiments an acceptable alignment of two nucleic acids comprises at least a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% A identity. Parameters and thresholds (e.g., a percent identity thresholds) for an acceptable alignment or match can be predetermined by a user, module or program. In some embodiments, an alignment comprises a mismatch (non-identical aligned nucleotides). In some embodiments, an alignment comprises 1, 2, 3, 4 5 or more mismatches. Two or more sequences can be aligned using either strand. In certain embodiments a nucleic acid sequence is aligned with the reverse complement of another nucleic acid sequence.

NGS sequencing methods often comprise various computational methods (e.g., computer implemented methods) which are used to map and/or align sequence reads to reference sequences (e.g., reference genomes). Sequence reads can be mapped by a mapping module or by a machine or computer comprising a mapping module (e.g., a suitable mapping and/or alignment program), which mapping module generally maps reads to a reference genome or segment thereof. Sequence reads and/or paired-end reads are often mapped to a reference genome by use of a suitable mapping and/or alignment program non-limiting examples of which include BWA (Li H. and Durbin R. (2009) *Bioinformatics* 25, 1754-60), Novoalign [Novocraft (2010)], Bowtie (Langmead B, et al., (2009)*Genome Biol.* 10:R25), SOAP2 (Li R, et al., (2009) *Bioinformatics* 25, 1966-67), BFAST (Homer N, et al., (2009) *PLoS ONE* 4, e7767), GASSST (Rizk, G. and Lavenier, D. (2010) *Bioinformatics* 26, 2534-2540), and MPscan (Rivals E., et al. (2009) *Lecture Notes in Computer Science* 5724, 246-260), or the like. Sequence reads and/or paired-end reads can be mapped and/or aligned using a suitable short read alignment program. Non-limiting examples of short read alignment programs are BarraCUDA, BFAST, BLASTN, BLAST, BLAT, BLITZ, Bowtie (e.g., BOWTIE 1, BOWTIE 2), BWA (Li H, D. R., Fast and accurate short read alignment with Burrows-Wheeler transform. (2009), *Bioinformatics,* 26 (5), 589-95), CASHX, CUDA-EC, CUSHAW, CUSHAW2, drFAST, FASTA, ELAND, ERNE, GNUMAP, GEM, GensearchNGS, GMAP, Geneious Assembler, iSAAC, LAST, MAQ, mrFAST, mrsFAST, MOSAIK, MPscan, Novoalign, Novoalign3, NovoalignCS, Novocraft, NextGENe, Omixon, PALMapper, Partek, PASS, PerM, PROBEMATCH, QPalma, RazerS, REAL, cREAL, RMAP, rNA, RTG, Segemehl, SeqMap, Shrec, SHRiMP, SLIDER, SOAP, SOAP2, SOAP3, SOCS, SSAHA, SSAHA2, Stampy, SToRM, Subread, Subjunc, Taipan, UGENE, VelociMapper, TimeLogic, XpressAlign, ZOOM, the like, variations thereof or combinations thereof. A mapping module can map sequencing reads by a suitable method known in the art or described herein. In some embodiments, a mapping module or a machine or computer comprising a mapping module is required to provide mapped sequence reads. A mapping module often comprises a suitable mapping and/or alignment program or algorithm.

Related Pathogens

Pathogens, due in part to their replication rate, can evolve at an accelerated rate compared to, for example, mammals. Accordingly, genetic variations are often introduced into the genome of pathogens at a high frequency of occurrence. Such genetic variations can be used to determined phylogenic relationships of a species of pathogen that evolves and/or mutates over a period of time, thereby determining ancestral relationships of child pathogens that were derived from a parental source.

Nucleic acid sequence data obtained by NGS methods can be used to quickly identify a pathogen species by comparing sequence data to reference databases that include nucleic acid sequence data for a multitude of pathogenic species. Mapping and/or aligning sequences (e.g., sequence reads) to a reference sequence (e.g., a reference genome) can also be used to identify genetic variations (e.g., single nucleotide variations (e.g., point mutations, single nucleotide polymorphisms (SNPs), deletions, insertions, copy number variations, and the like) within a genome of a pathogen. Using methods that comprise NGS sequencing, genetic variations can quickly be determined within a genome of a pathogen and such genomic sequence data can be used to identify pathogens to the sub-species and strain level. Accordingly, nucleic acid sequence data is used to identify related pathogens, and in some embodiments, to construct a phylogenetic tree or graph that is used to identify a potential source pathogen as well as related child and/or sibling pathogens of a particular pathogen species. Pathogens of the same species that have the same or divergent genetic content are referred to herein as related pathogens. In certain embodiments, related pathogens are related strains of the same species.

In certain embodiments, the sequence information from one or more isolates is compared with sequence information from other samples taken from objects (e.g., patients, devices or caregivers in the hospital), both contemporaneous and historical, to determine a path of infection (e.g., if another patient may have inadvertently transmitted the disease). In certain embodiments, method of comparing sequence information of one or more microorganisms, method of identifying related organisms, methods of identifying commonalities between organisms and objects, and methods of determining transmission paths are described in International Patent Application No. PCR/EP2016/055195 (the '195 application) filed Mar. 10, 2016, (Publication No. WO/2016/142493) which is incorporated herein by reference in its entirety. In certain embodiments, the methods described in the '195 application are contemplated for use herein, and/or can be used in combination with the methods described herein to generate a transmission metric. In certain embodiments, a method of identifying related pathogens is described in International Patent Application No. PCT/IB2016/054139 (the '139 application) filed Jul. 11, 2016, which is incorporated herein by reference in its entirety. In certain embodiments, the methods described in the '139 application are contemplated for use herein, and/or can be used in combination with the methods described herein to generate a transmission metric.

Single nucleotide variations (SNVs) are also used to identify related pathogens. Single nucleotide variations (SNVs) (e.g., point mutations, SNPs) are single-nucleotide differences in a genetic sequence of the genome of a pathogen. Hundreds to thousands, or even millions of SNVs may exist in a genome of a pathogen species. SNVs can occur anywhere in a genome of a pathogen at anytime. Loci where SNPs occur are often known and/or mapped. A SNP typically has only one of two different variants (e.g., C or A, A or T, G or C, etc.). SNPs may occur in both coding and non-coding DNA sequences and are useful markers of variation and evolutionary divergence in microbial genomes.

In certain embodiments, a collection of sequence data identifying genetic variations within isolated pathogens is used to generate a genetic variation score for each pathogen. Any suitable computer implemented method can be used to determine a genetic variation score. In certain embodiments, genomic sequence data comprises a genetic variation score, or sequence data for multiple genetic variations within a genome of a pathogen. A genetic variation score is, in some embodiments, used to identify related pathogens (e.g., a set of related pathogens). In some embodiments, a genetic variation score comprises an SNP differences.

In certain embodiments, a collection of SNP data comprising the identification of resident nucleotides at multiple SNP loci with the genome of a pathogen species is referred to herein as SNP differences. Any suitable computer implemented method can be used to determine SNP differences. In certain embodiments, genomic sequence data comprises SNP differences, or sequence data for multiple SNPs within a genome of a pathogen. Such genomic sequence data, in some embodiments, is used to identify related pathogens (e.g., a set of related pathogens). Related pathogens are often pathogens of the same species. In some embodiments, related pathogens are related strains of the same species.

In certain embodiment, related pathogens are identified according to one or more differences or similarities within genomic regions comprising tandem repeats. For example, within certain species of microbial pathogens, certain loci have been identified that include regions having a variable number of tandem repeats. Using NGS sequencing methods, the number of tandem repeats at a particular locus of a pathogen's genome can be counted. By counting tandem repeats at multiple loci, one of skill in the art can often identify related strains (e.g., parents or children) of a pathogen species. In certain embodiments, quantitative analysis of multiple tandem repeat loci is performed by a method comprising Multiple-Locus Variable Number Tandem Repeat Analysis (MLVA).

Provided herein are, in some embodiments, methods of identifying a set of related pathogens according to a relationship between the genomic sequence data obtained from two or more pathogens. A relationship between the genomic sequence data of two or more pathogens can be determined by comparing the genomic sequence data using any suitable method. For example, a relationship between the genomic sequence data of two or more pathogens can be determined by comparing SNP patterns at multiple loci within the genome of the two or more pathogens, comparing SNP differences of the two or more pathogens, comparing tandem repeats counts at multiple loci within the genome of the two or more pathogens, comparing MLVA data for the two or more pathogens, or a combination thereof. Additional data, non-limiting examples of which include antibiotic resistance, growth requirements, growth rate, mutation rate, microscopic and macroscopic features, temporal relationship of clinical data and symptoms observed in infected patients, can also be used to identify related pathogens. In certain embodiments, additional data comprises a host response to a pathogen infection (e.g., a host phenotype, symptoms), which data can be used to disambiguate transmission chronology for pathogens showing very few genomic differences (e.g., SNP differences). Accordingly, genomic sequence data can used alone or in combination with such additional data, to establish phylogenetic trees and to identify related pathogens. For example, a set of related pathogens can be identified, in part, by determining and/or comparing the growth rates of two or more pathogens.

Given a known or estimated replication rate and/or a known or estimated mutation rate, a temporal relationship between two related strains can sometimes be determined. In some embodiments, the presence of additional differences in the genomic sequence data between two pathogens is evidence of a more distant phylogenetic relationship. In certain embodiments, little or nor difference in the genomic sequence data between two pathogens of the same species indicates that the two pathogens are the same or highly related.

In some embodiments, a set or subset of related pathogens is determined. In certain embodiments, a set or subset of related pathogens is identified by identifying that two or more pathogens are derived from the same species. In certain embodiments, a set or subset of related pathogens is identified by identifying that two or more pathogens are derived from the same sub-species or strain. In some embodiments, a set or subset of related pathogens is identified at a strain level according to an antibiotic resistance. For example, two or more pathogens may be identified as related strains by way of being identified as a certain ESKAPE pathogen (e.g., *S. aureus*) that is resistant to tetracycline. A phylogenetic relationship between the two strains can sometimes be determined according to genomic sequence data and for example, by comparing the SNP differences of the two pathogens. In some embodiments, a comparison of SNP differences between two pathogens can determine that a second pathogen is derived from a first related pathogen. In certain embodiments, two related pathogens are identified by a method comprising MLST typing. In certain embodiments, two or more related pathogens are identified by a method comprising comparing gene expression signatures. In some embodiments, identifying a set of related pathogens comprises determining a pathogen's closest neighbor.

In some embodiments, genomic sequence data of one or more pathogens is compared to a reference genome. A reference genome can be a reference sequence for a pathogen species or strain. In certain embodiments, a reference genome is determined from a set of pathogens (e.g., set of pathogen tags) identified from samples obtained over a period of time from one or more defined locations. For example, a reference genome is sometimes determined from a set of pathogens (e.g., set of pathogen tags) identified from samples obtained over a period of time (e.g., 1-2 years) from a hospital. For example, frozen samples comprising bacteria obtained from various locations within a hospital over a period of time, can be thawed, cultured, analyzed and/or sequenced (thereby generating pathogen tags) and the genomic information obtained from the samples can be compared to the genomic information of a recent sample comprising a bacteria identified as a pathogen (e.g., a recent pathogen tag). The genomic information of any suitable pathogen or pathogen tag can be used as a reference (e.g., a reference genome). For example, a dominant MLST within a set of samples can be used as a reference genome.

In some embodiments, identifying a set of related pathogens comprises determining a pathogen's mutation rate. In some embodiments, identifying a set of related pathogens comprises determining a pathogen evolutionary distance between two or more pathogens. Often, in certain embodiments, identifying a set of related pathogens comprises generating a phylogenetic metric or phylogenetic tree according to genomic sequence data and other additional pathogen data, alone or in combination. In some embodiments, a set of related pathogens comprises or consists of a species of ESKAPE pathogens. The term "ESKAPE" pathogens refers to any one of six pathogens: *Enterococcus faecium, Staphylococcus aureus, Klebsiella pneumoniae, Acinetobacter, Pseudomonas aeruginosa* and *Enterobacter*, which species are sometimes associated with multidrug resistant virulence.

In certain embodiments, a transmission path of related pathogens in determined according to the transmission metric. In some embodiments, a parent pathogen is identified according to a transmission path.

The term "percent identical", "% identical" or "percent identity" refers to sequence identity between two polynucleotide sequences. Identity can be determined by comparing a position in each sequence which may be aligned for purposes of comparison. When an equivalent position in the compared sequences is occupied by the same nucleotide, then the molecules are identical at that position. When the equivalent site is occupied by the same or a similar nucleotide, then the molecules can be referred to as homologous (similar) at that position. Expression as a percentage of homology, similarity, or identity refers to a function of the number of identical or similar nucleotides at positions shared by the compared sequences. Expression as a percentage of homology, similarity, or identity refers to a function of the number of identical or similar nucleotides at positions shared by the compared sequences. Any suitable algorithm or program can be used to determine homology, similarity or identity. Non-limiting examples of alignment algorithms and/or programs that may be used to determine homology, similarity and/or identity include FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each nucleotide gap is weighted as if it were a single nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

In some embodiments one or more sequence reads and/or information associated with a sequence read are stored on and/or accessed from a non-transitory computer-readable storage medium in a suitable computer-readable format. Information stored on a non-transitory computer-readable storage medium is sometimes referred to as a file or data file. Genomic sequence data, reads, selected reads, sets or subsets of reads and/or information associated with one or more reads is often stored in a suitable file or suitable data file. Genomic sequence data can be stored locally or remotely, for example in one or more local servers, one or more remote servers or in a cloud based system. In certain embodiments, genomic sequence data associated with a pathogen tag or proximity tag can be retrieved and/or accessed locally or remotely, for example from one or more local servers, from one or more remote servers or from a cloud based system.

Proximity Tags

In certain embodiments a proximity tag is provided. In some embodiments a plurality of proximity tags is provided. In certain embodiments, a pathogen tag refers to electronic information associated with or related to an object. In some embodiments, a proximity tag is a collection of information stored in the form of non-transitory computer-readable storage medium (e.g., a file, a packet). In certain embodiments, a proximity tag, or portions thereof, can be transferred to and/or from one or more computer modules, systems, processors, servers, storage mediums, and the like, and may be transformed into a visual display (e.g., a monitor, an interactive visual display) or printed. In certain embodiments, a proximity tag comprises information about an object and often includes a unique object identifier associated with a single object (e.g., device, subject, patient, medical professional). A plurality of proximity tags can be provided, wherein each of the proximity tags is associated with the same object and/or the same object identifier. Accordingly, a unique identifier is often unique to an object. Further, a plurality of proximity tags can be provided for a plurality of different objects. A unique identifier can be any suitable identifier, non-limiting examples of which include a name (e.g., a subject name, a device name), any suitable alpha-numerical identifier, a social security number, a patient ID, insurance ID, an electronic medical records ID, the like or combinations thereof. A unique identifier can be encrypted or non-encrypted. In certain embodiments, a unique identifier is encrypted and is only accessible by authorized users.

In some embodiments, a proximity tag comprises a subset of data or information associated with an object. In certain embodiments, a proximity tag comprises a probable coordinate. In certain embodiments, a probable coordinate defines a location, or location history of an object within one or more defined regions within a period of time. A location can be an exact location or probable location. A location of a mobile object may also be associated with a time period. A coordinate can be a two-dimensional coordinate or a three-dimensional coordinate. In certain embodiments, a coordinate of a proximity tag is a three-dimensional coordinate. A probable coordinate can be, in some embodiments, an exact coordinate, for example, where an exact location of an object is known and/or verified at a specific period of time. In certain embodiments, a probable coordinate is a probability that an object was present at a defined location at, or within, a specified period of time. For example, where an object is a fixed object within a building, the location of the object is know to be at an exact coordinate at any one specific time. Where an object is a device, for example a mobile medical device such as a blood pressure machine mounted on wheels, a first proximity tag associated with the device, in certain embodiments, can verify an exact location of the device within a certain surgical suite on floor 3 of hospital 1, at a time period between noon and 6 p.m. on a certain date. A second proximity tag associated with the same device, in certain embodiments, can verify an exact location of the device within a certain emergency room on floor 3 of hospital 1, at a time period between 8 p.m. and 10 p.m. on the same date. A third proximity tag for the same device, in certain embodiments, can provide a probable coordinate (e.g., a high probability), indicating that the device was located somewhere on floor 3 of hospital 1 between 6 p.m. and 8 p.m. on the same day. In yet another example, where an object is a patient who checks in at hospital 1 at 8 a.m. on a certain day and checks out at 10 a.m. on the same day, a proximity tag is provided indicating a probable coordinate of the patient within hospital 1 between 8 am and 10 a.m. If the same patient has a scheduled office visit with Dr. Jones at 8:30 a.m., in suite C on that same day, another proximity tag is provided indicating an exact location of the patient in suite C at 8:30 a.m. Further, a proximity tag is generated for Dr. Jones indicating an exact location in suite C at 8:30 a.m. Accordingly, a transmission metric generated by a method herein can identify an intersect between the patient and Dr. Jones at the same location on the same day according to the proximity tags provided.

In some embodiments a proximity tag is generated for, assigned to, or associated with a patient, a caregivers, or any objects present in a defined area. For example, within a hospital premises a proximity tag can be generated for, assigned to, or associated with housekeeping staff, visitors, maintenance staff, drivers, contract workers, clerical and administrative staff, as well as caregivers, patients and devices.

In certain embodiments, one or more proximity tags are created, generated, tracked and or stored by a system or process comprising a real time location system (RTLS) or real time location service. In certain embodiments, one or more RTLS systems can be used to generate, track, collect and store proximity tags for objects, including people and devices. In some embodiments, a proximity tag is generated for a patient and/or caregiver when a care transaction is determined. For example, a clinical or HIT system can generate a proximity tag for a patient and a caregiver when a patient is admitted from the ED to a specific patient room, or when caregiver x performs a procedure Y in location z, for example.

In certain embodiments, a proximity tag comprises clinical information regarding a patient (e.g., an object who is a patient) non-limiting examples of which include a diagnosis, health history, health status, infection status, symptoms, treatment, prognosis, physicians visited, check-in times, check-out times, treatment rooms visited, patient name, patient ID, the like, and combinations thereof.

A period of time can be an exact time or may be a range of times. For example, a period of time can be 5 p.m. on Jul. 9, 2015. In yet another example, a period of time can be between 5 p.m. on Jul. 9, 2015 and 3 p.m. on Jul. 12, 2015. Accordingly, in certain embodiments, a period of time is a specific day, hour, and/or minute. In some embodiments, a period of time is a time range of one or more minutes, hours, days, weeks, months or years. Where an object is fixed within a building, a time period for a proximity tag for that object may be years or more.

Pathogen Tags

In certain embodiments a pathogen tag is provided. In some embodiments a plurality of pathogen tags are provided. In certain embodiments, a pathogen tag refers to electronic information associated with or related to a pathogen. In some embodiments, a pathogen tag is a collection of information stored in the form of non-transitory computer-readable storage medium (e.g., a file, a digital packet). In certain embodiments, a pathogen tag, or portions thereof, can be transferred to and/or from one or more computer modules, systems, processors, servers, storage mediums, and the like, and may be transformed into a visual display (e.g., a monitor, an interactive visual display) or printed. In certain embodiments, a pathogen tag comprises a proximity tag. In some embodiments, a proximity tag comprises a pathogen tag. In certain embodiments, a pathogen tag comprises information about a pathogen and often includes a unique pathogen identifier associated with a pathogen, or sample from which a pathogen is obtained or isolated. In some embodiments, a plurality of pathogen tags can be provided, wherein each of the pathogen tags is associated with related or unrelated pathogens. A unique pathogen identifier can be any suitable identifier, non-limiting examples of which are a name (e.g., a pathogen genus, species, and/or strain), any suitable alpha-numerical identifier, genomic finger print, bar code, the like or combinations thereof. A unique pathogen identifier can be encrypted or non-encrypted. In certain embodiments, a unique pathogen identifier is encrypted and is only accessible by authorized users.

Pathogens are often obtained from a sample which is obtained from an object. Accordingly, in certain embodiments, a pathogen tag comprises a proximity tag associated with an object. In some embodiments, a proximity tag associated with a pathogen tag provides information about where and when a pathogen was obtained or isolated. In some embodiments, a proximity tag associated with a pathogen tag provides a probable coordinate defining a location of the object from which a pathogen (or sample comprising a pathogen) was obtained. In some embodiments, a proximity tag associated with a pathogen tag provides a period of time in which a pathogen (or sample comprising a pathogen) was obtained. For example, a pathogen tag often comprises a proximity tag having a unique identifier for a subject from which a sample was obtained, where the sample was later determined to comprise the pathogen, and information indicating the location of the patient and time period when the sample was obtained. In some embodiments, a pathogen tag comprises a subset of data or information associated with a pathogen.

In one non-limiting example, a sample is obtained from an object, where the sample comprises nucleic acid and the sample is subjected to an analysis comprising NGS sequencing. The resulting nucleic acid reads are analyzed and compared to reference sequences (e.g., genomic sequence data of other pathogen tags) to determine if a pathogen is present. When a pathogen is deemed present, a first pathogen tag is provided or generated which tag comprises genomic sequence data for the first pathogen, a unique pathogen identifier and a proximity tag associated with the object from which the pathogen was obtained. In certain embodiments where the first pathogen tag is associated with a first proximity tag (e.g., for an object, a subject, or mobile object), additional pathogen tags may be generated, which newly generated pathogen tags are associated with, linked to or comprise other proximity tags having the same unique object identifier as the first proximity tag. Such additional pathogen tags may include a proximity tag indicating a period of time and location (e.g., probable coordinate) where an infected subject or device was present (e.g., at a time before, or after isolation of the sample comprising the first pathogen). In some embodiments, a notification is immediately triggered to remove a device that is associated with a pathogen tag from service. In some embodiments, a notification is immediately triggered and sent to a medical professional notifying them of the presence of a patient infected with the first pathogen. Generation of a pathogen tag, in some embodiments, triggers a process wherein other related pathogens are identified, according to a comparison of genomic sequence data and other species or strain information retained in a pathogen tag. In some embodiments, identification of two or more related pathogens triggers (e.g., within a computer implemented system) recruitment of some or all related pathogen tags and/or initiates a process of generating a phylogenetic metric or tree. In some embodiments, related pathogens are identified according to a phylogenetic metric or tree.

In some embodiments, pathogens (e.g., related pathogens) are associated with a transmission tree, where nodes of the tree are organized based on clinical data driving disambiguation for low SNP difference scores.

A phylogenetic metric refers to any suitable phylogenetic relationship or phylogenetic tree. A phylogenic metric or phylogenetic tree can be generated by using any suitable method. In some embodiments, a phylogenetic metric is a phylogenetic graph. For example, exemplary methods of generating a phylogenetic tree and identifying relationships is provided in International Patent Application Publication No. WO/2016/024213, which in incorporated herein by reference. Multiple phylogenetic methods exist, including methods based on evolutionary distances, parsimonious, and maximum likelihoods. Distances based methods determine an evolutionary distance between each organism. An evolutionary distance is sometimes calculated based on the degree of similarity between genetic sequences of organisms. One such method for determining evolutionary distances is called the Jukes-Cantor (*Evolution Of Protein Molecules In Mammalian Protein Metabolism*, Vol. III (1969), pp. 21-132 by T. H. Jukes, C. R. Cantor edited by M. N. Munro), which in incorporated herein by reference. In certain embodiments, rates of evolution may be determined by a suitable method. In certain embodiments, generating a phylogenetic metric or tree and identifying related pathogens (or subsets thereof) comprises determining evolutionary distances and relationships between pathogens and/or plotting said distances and/or relationships in graphical form (e.g., a tree plot). In certain embodiments, phylogenetic metrics and/or phylogenetic trees can be generated and used to identify related pathogens using suitable methods described in Saitou N, Nei M., "*The Neighbor-Joining Method: A New Method For Reconstructing Phylogenetic Trees*", (1987) Molecular Biology and Evolution, volume 4, issue 4, pp. 406-425; Britton, Tom, et al., "Phylogenetic dating with confidence intervals using mean path lengths" (2002) Molecular Phylogenetics and Evolution 24.1: 58-65; and/or International Patent Application Publication No. WO/2016/051298. In certain embodiments, related pathogens are identified by a process comprising a Random Walk or weighted Markov Chains.

In certain embodiments a proximity tag and/or a pathogen tag can be transformed into an interactive digital image on a display, for example, represented as a node. In some embodiments, an image includes a time history of encounters of proximity tags for a segment of the phylogeny or transmission tree. In some embodiments, a user (e.g., a remote user) of a system described herein, can access a proximity tag, as well as some or all information included in a proximity tag, by selecting (e.g., by mouse click, stylus or finger selecting) on an interactive node (e.g., an image, an icon) on a display, where such node represents a proximity tag.

Transmission Metrics

In certain embodiments, a transmission metric is provided or generated herein. A transmission metric, in certain embodiments, is generating according to a plurality of proximity tags and/or pathogen tags for a plurality of related pathogens. In certain embodiments, a transmission metric comprises a transmission graph. For example a transmission graph may include only subject nodes. In some embodiments, a transmission graph includes only patient nodes, only caregiver nodes, or only patient and caregiver nodes. In certain embodiments, a transmission metric comprises a correlate graph. In some embodiments, a correlate graph includes subject nodes and pathogen nodes. A transmission graph can be, in some embodiments, an interactive transmission graph. In certain embodiments, a transmission graph comprises a correlate graph. In some embodiments, a transmission metric comprises one or more nodes and one or more edges. In some embodiments a node comprises a pathogen tag. In some embodiments, a node comprises a proximity tag. In certain embodiments a node comprises one, two, three, four or more proximity tags, pathogen tags or a combination thereof. In certain embodiments, a node represents an intersect between two or more proximity tags and/or pathogen tags (i.e. tags). An intersect, in certain embodiments, is an overlap between two or more tags, where there is a likelihood, probability or confirmation that an object of two or more tags shared an overlap of a period of time and a probable coordinate. In some embodiments, an edge comprises an intersect. A node is often a representation one or more relationships between a subset of related pathogens, a subset of objects associated with said related pathogens, probable periods of time and probable coordinates. The method of embodiment A1, wherein the transmission metric comprises interactive nodes and edges presented on a display, each node comprising a pathogen tag or a proximity tag, and each edge comprising a probability of transmission.

In certain embodiments the genomic sequence data comprises one or more single nucleotide variants (SNVs) or single nucleotide polymorphisms (SNPs) relative to a known reference genome or the entire genome sequence of the pathogen which can be constructed by either aligning sequence reads to a known reference genome, using genome assembly techniques, or a hybrid approach. When multiple pathogens have been sequenced the genome sequences from the samples can be compared to count the number of SNV differences between 2 pathogen sequences. In one embodiment, we can measure genomic similarity by examining all single nucleotide variants (SNVs), but other embodiments may measure genomic similarity by only considering SNPs (which are SNVs that occur in at least two samples). Furthermore, genomic similarity can be measured more broadly by also considering other genetic differences (e.g., mutational differences), including but not limited to, insertions, deletions, inversions, rearrangements, tandem repeats, and copy number variations between samples. By examining these mutational differences we can define a metric to measure the differences between the samples. In the simplest embodiment, this mutational difference score may simply be the number of SNV differences between two samples, but more complicated versions may compute a difference score based on a weighted sum of the differences observed between samples in the categories of mutational differences mentioned above.

Figure 12A:
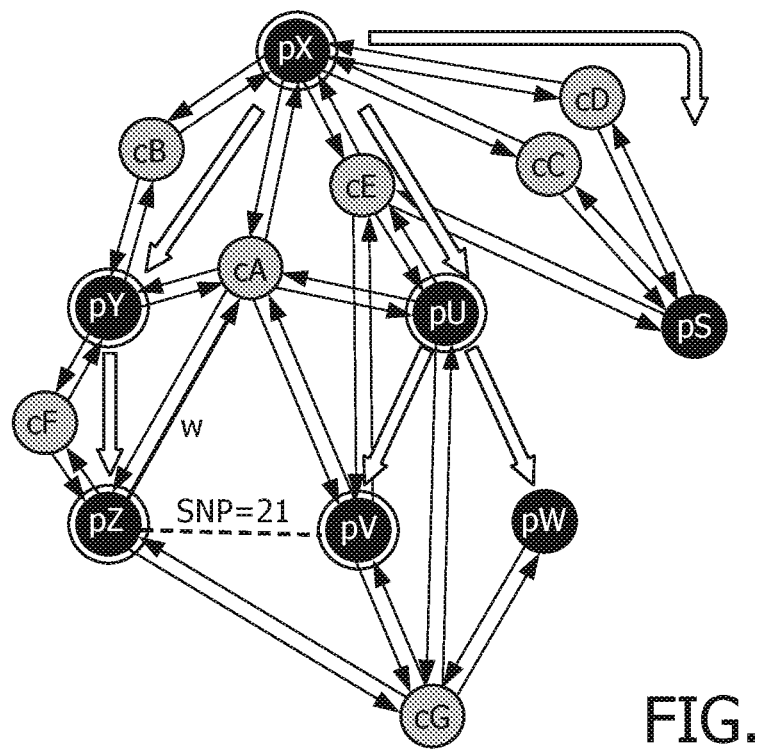
FIG. 12A shows that the pathogen of pZ and the pathogen of pV have 21 SNP differences. Accordingly SNP=21 differences and an inverse SNP difference of $1/21$.
Figure 12B:
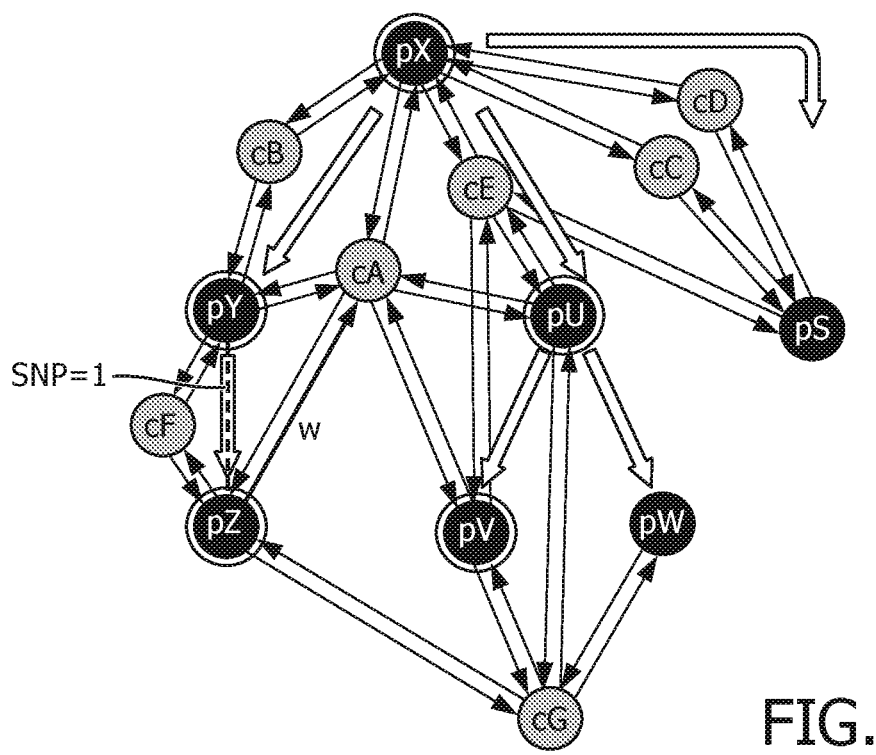
FIG. 12B shows that the pathogen of pZ and the pathogen of pY have 1 SNP difference.
Figure 12C:
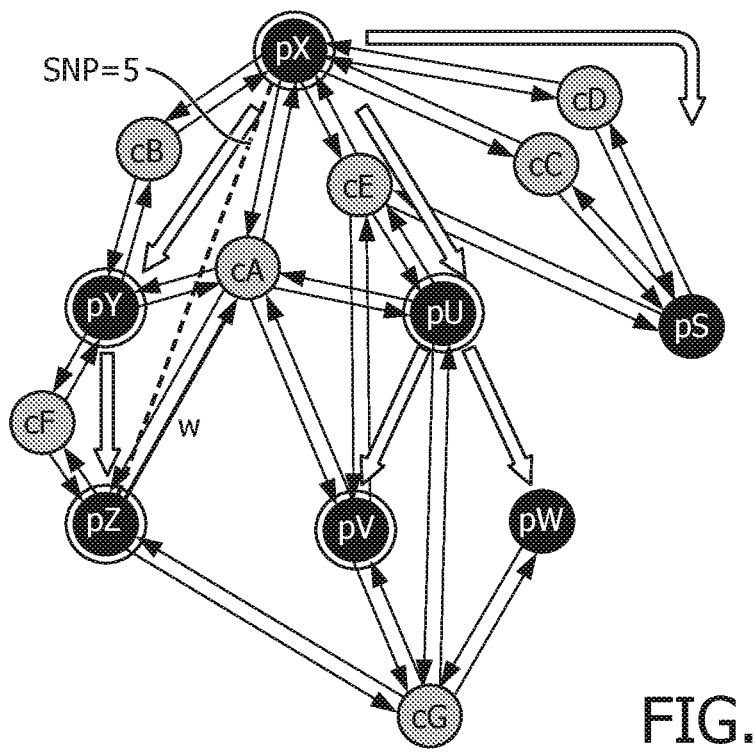
FIG. 12C shows that the pathogen of pZ and the pathogen of pX have 5 SNP differences.
Figure 12D:
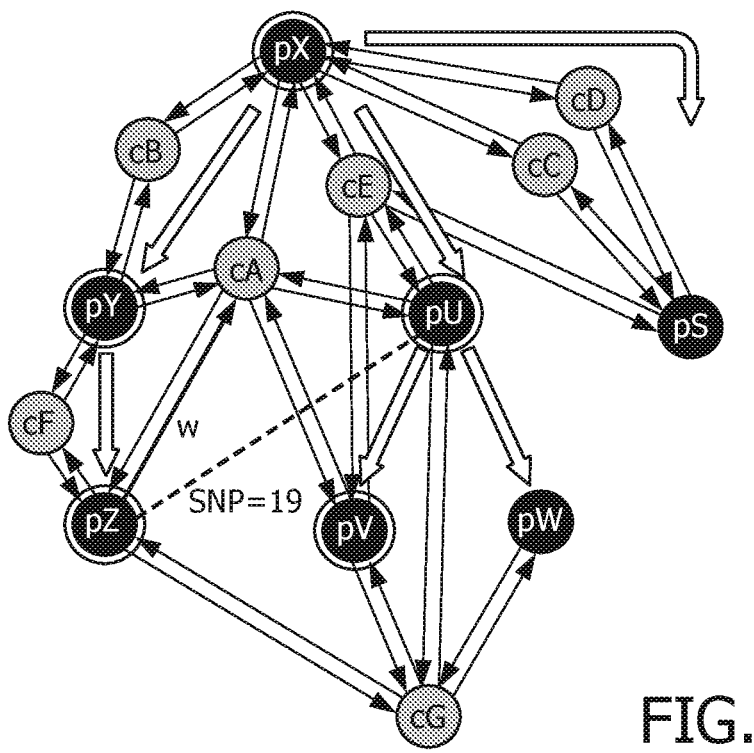
FIG. 12D shows that the pathogen of pZ and the pathogen of pU have 19 SNP differences. Accordingly, the weight of edge W is determined by the formula $W=1/21+1/1+1/5+1/19$ and the weight of edge W equals 1.3 as shown in FIG. 12E. In certain embodiments, the weighting of edge W is then normalized so all outgoing weights from each patient node adds up to 1 (e.g. edge weights pZ to cG, pZ to cA, and pZ to cF add up to 1 as seen in FIG. 13A). In this particular example, the normalized weighted value of edge W equals 0.53 as shown in FIG. 12F. The weighting process can then be applied to all incoming and outgoing edges for caregivers and patients.
Figure 12E:
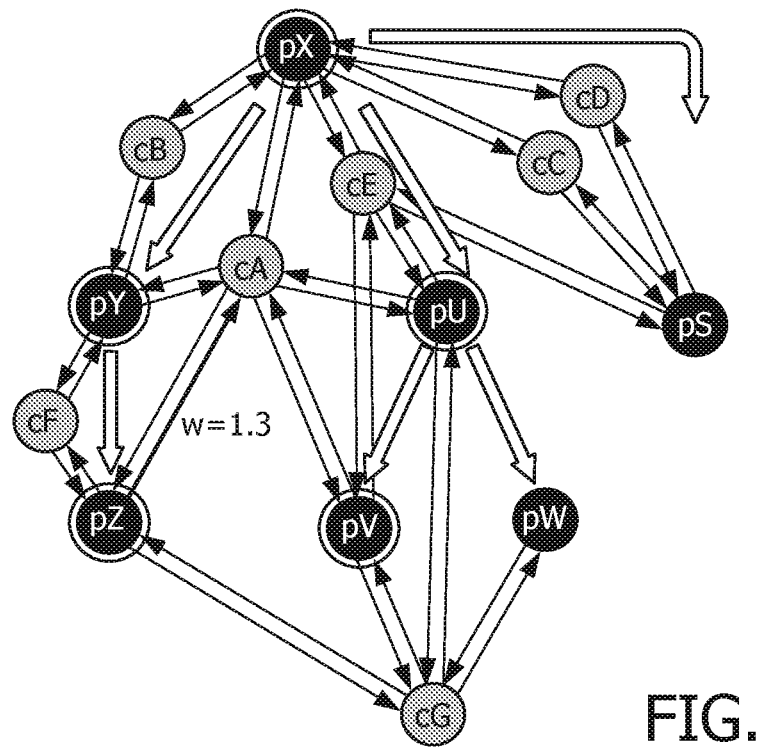
FIG. 12 illustrates a novel process for determining an edge weight (W) based on phylogenetic differences (or similarities) between highly related pathogen strains isolated from patients (e.g., pS, pU, pV pW, pX, pY, and pZ) and caregivers (e.g., cA, cB, cC, cD, cE, cF and cG). In this embodiment, weighting is determined, in part, according to SNP differences of a subset of SNPs for the related pathogen strains where the weight for each patient edge (e.g., W) is the sum of the inverse of SNP differences between the pathogen obtained from pZ and pathogens obtained from each patient (e.g., pX, pY, pU, and pV) connected to caregiver cA. For example.
Figure 12F:
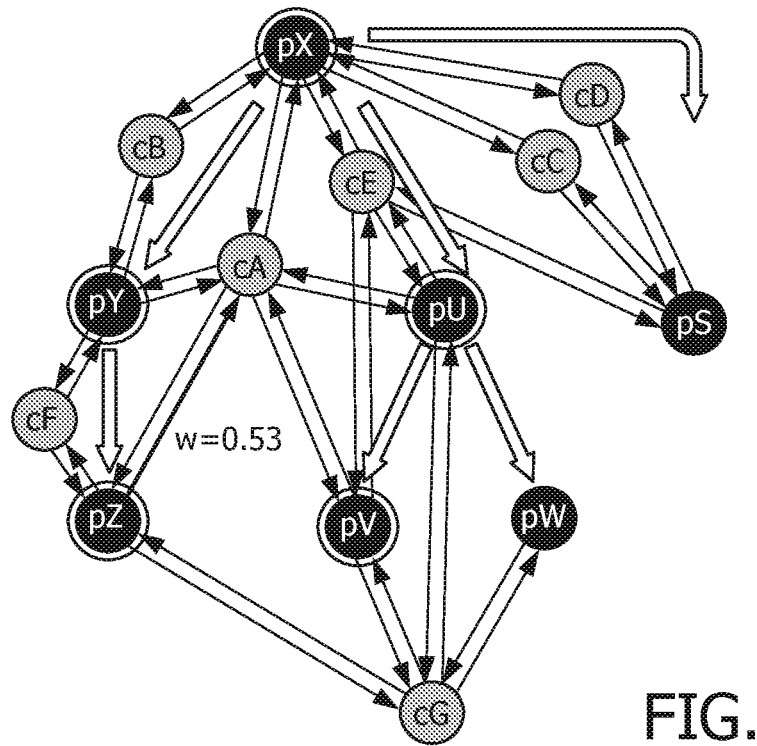
Figure 13A:
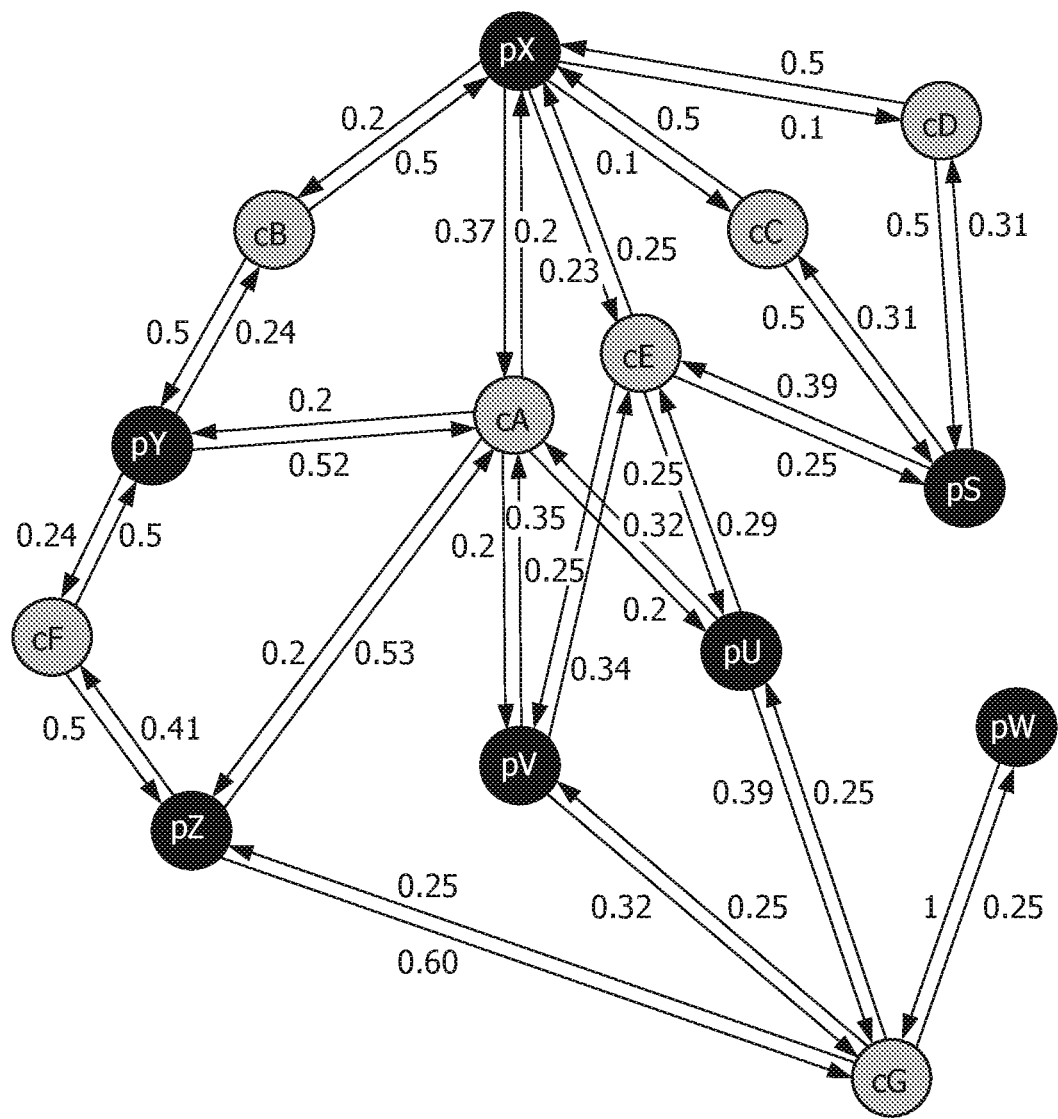
FIG. 13A shows an embodiment of a transmission metric where normalized weighted values are determined for all incoming and outgoing edges as described in the example of FIG. 12.

In certain embodiments, a transmission metric is generated using a novel weighting process that can provide edge weights between nodes based on, for example, pathogen relatedness (e.g., SNP differences/similarities), and/or proximities (e.g., physical distances between objects). For example, within a defined location (e.g., a hospital) biological samples may be obtained from several objects (caregivers, devices, patients) wherein genetic and/or microbiological analysis determines that a subset of samples all contain related pathogen (e.g., same species, or related strains). A transmission metric can then be generated where each node in the metric represents an object (e.g., an object comprising a pathogen tag). Note that a pathogen tag or object may, or may not be associated with a proximity (e.g., a location). In some embodiments, it is known, for example from input data collected (e.g., see system of FIG. 1) that certain objects in the transmission metric were in contact (e.g., confirmed contact or probable contact) at some point in time (e.g., within a selected time period). Edges between nodes can then be weighted and/or ranked by a novel process described herein. For example, edge weights can be determined according to SNP differences for pathogens of each node (e.g., see FIG. 12). In some embodiment, edge weighting is determined according to SNP differences where the weight for each edge between a central node (a first object) and all nodes that contacted, or were suspected of contacting the central node (probable contacts), is the sum of the inverse of SNP differences between the pathogen of the central node and the pathogens of each contacted node. For example, FIG. 12A shows that the pathogen of pZ and the pathogen of pV have 21 SNP differences. Accordingly the SNP differences equal 21 and the inverse SNP difference is $1/21$. FIG. 12C shows that the pathogen of pZ and the pathogen of pX have 5 SNP differences and the inverse SNP difference is therefore $1/5$. Accordingly, the weight of edge W (FIG. 12) is determined by the equation $W=1/21+1/1+1/5+1/19$ and the weight of edge W equals 1.3 as shown in FIG. 12E. In certain embodiments, the weighting of edge W is then normalized so all outgoing weights from each patient node adds up to 1 (e.g. edges weights pZ to cG, pZ to cA, and pZ to cF add up to 1 as seen in FIG. 13A). In this particular example, the normalized weighted value of edge W equals 0.53 as shown in FIG. 12F. The weighting process can then be applied to all incoming and outgoing edges for all nodes in a transmission metric. In certain embodiments, weighting comprises a process utilizing a Random Walk or weighted Markov Chains method based on SNV or SNP differences or similarities.

In certain embodiments edges can weighted according to proximities. For example edges between nodes (each representing a proximity tag for an object) can be weighted between actual or probable distances between objects. It is known that certain pathogens can be transmitted by direct contact as well as by airborne mechanisms. Accordingly, when determining a transmission metric it is often important to take into account a distance between a potential vector (e.g., a person harboring a contagious pathogen) and another person or device that may have obtained the pathogen from the vector. Methods of determining a transmission path of a pathogen may take into account a direct contact between objects or physical distances between objects. Methods described herein can weight edges between nodes of a transmission metric using distances between objects. Distances can be expressed in any suitable manner, non-limiting examples include a distance between two or more objects within a plane (2-dimensional coordinate system), distance between two objects in 3 dimensional space (e.g., where locations are expressed as Cartesian coordinates), or an array of locations in Euclidian space. For example, methods described herein can weight an edge between two nodes of a transmission metric based on the fact that a potential vector (e.g., a first node, a person harboring a contagious pathogen) was present at a location within 12 vertical feet of another person (e.g., a second node, a person determined to be infected with a related pathogen). For example the potential vector (first node) was determined to be present in a treatment room on the $4^{th}$ floor directly above a treatment room on the $3^{rd}$ floor where the other person (e.g., second node) was determined to be present, and the two rooms share a common air vent. Accordingly, in certain embodiments, edges between nodes are weighted according to distances between objects within a three dimensional space.

For example, for each outgoing edge of a node (first location) to another node (another location), the weight is provided as the inverse of the distance between nodes. The process is similar to the method of weighting an edge based on SNP differences. If the distance between to node locations is zero, the 0 value can be replaced by $\frac{1}{10}$ of a minimum non-zero distance. Alternatively, a 0 value can be replaced by $\frac{1}{2}$ to $\frac{1}{10,000}$ or a minimum non-zero distance. Alternatively, a 0 value can be replaced by $\frac{1}{20}$, $\frac{1}{50}$ or $\frac{1}{100}$ or less of a minimum non-zero distance. A minimum non-zero distance can be predetermined as an arbitrary value less than any other distance between nodes of a transmission metric. In some embodiments, a minimum non-zero distance is the smallest distance determined between a node and any other connecting node. In some embodiments, a distance or location value of a node may be absent or unknown. For a missing distance values, a value of 10 times the maximum distance between nodes of a transmission metric can be used. Alternatively, a value of 2 to 1000 times the maximum distance between nodes can be used. Alternatively, a value of 2 times, 5 times, 10 times, 50 times, 100 times, or more, of the maximum distance between nodes can be used.

In some embodiments, edges are weighted according to time. For example, for an edge between to nodes (e.g., representing two objects) present at the same location within a period of seconds is given more weight than an edge between two nodes that are separated by a period of hours or days. The process is similar to the method of weighting an edge based on distances.

Accordingly, edges between nodes of a transmission metric can be weighted according to pathogen relatedness (e.g., SNP differences), distance (e.g., location), and/or time. For example, in certain embodiments edges between nodes of a transmission metric are weighted according to pathogen relatedness and distance, pathogen relatedness and time, distance and time or pathogen relatedness, distance and time. For example, as illustrated in FIG. 15, edges can be weighted using SNP differences (FIG. 15B), using location distances (FIG. 15C) or using a combination of edge weighting using SNP differences and location distances (FIG. 15D). In some embodiments, edge weighting is normalized. In some embodiments, edge weighting is not normalized.

In some embodiments, nodes are ranked or are provided a rank score or rank value. In some embodiments, node ranks are determined according to edge weights. Accordingly, the rank or rank value of each node is determined according to genetic similarities or differences of pathogens, location (e.g., relative locations of objects) and/or time. In some embodiments, node ranks are determined according to edge weights for some or all edges that contact a node. In some embodiments, node ranks are normalized. In some embodiments, node ranks are not normalized. In certain embodiments, nodes of a transmission metric are ranked using a modification of PageRank (e.g., retrieved from the Internet). The PageRank algorithm is website ranking tool used by website search engines (e.g., Google) and was modified herein to develop a novel, more accurate, and faster process of rank nodes of a pathogen transmission metric.

For example, using the novel weighting algorithm presented herein, 23,449 edges of a transmission metric comprising 1000 nodes (e.g., 800 caregivers and 200 patients) took about 416 milliseconds. The 1000 nodes were then ranked after 38 iterations, which ranking took a total of 28 milliseconds. Accordingly, the process of generating a transmission metric and ranking nodes as described herein is more informative and faster than traditional approaches.

In certain embodiments related pathogens of a set are identified according to a correlation between mutational differences (e.g., a mutational difference score) and a period of time (e.g., time elapsed between sample isolation for two or more pathogen samples). In certain embodiments edges between two nodes (e.g., between two pathogen tags) are weighted according to a correlation between mutational differences (e.g., a mutational difference score) and a period of time (e.g., time elapsed between sample isolation for two or more pathogen samples). In some aspects related pathogens of the set are identified according to a correlation between one or more mutational differences and an expected mutation rate.

In certain embodiments related pathogens are identified by a process comprising a Random Walk or weighted Markov Chains. In certain embodiments, a random walk is used to provide a probability score for a correlate as being responsible for one or more transmissions, and correlates can be ranked according to the probability score. In certain embodiments the probabilistic correlations comprise probabilistic matches between the probable coordinates of two or more proximity tags and the probable coordinates of one or more of the related pathogen tags. In certain embodiments determining the presence of one or more relationships comprises determining one or more temporal relationships between one or more objects (e.g., proximity tags, pathogen tags). In certain embodiments the temporal relationships comprise one or more probable intersects between two or more proximity tags. In some embodiments identifying a set of related pathogens comprises a typing scheme, such as MultiLocus Sequence Typing (MLST), ribosomal MLST (rMLST), core genome MLST (cgMLST) and whole genome MLST (wgMLST), or identification of gene expression signatures, determining a pathogen's closest neighbor, determining a pathogen's mutation rate, determining pathogen growth rates, determining a pathogen's evolutionary distance between two or more other pathogens and/or generating a phylogenetic metric or phylogenetic tree. In the literature, phylogenetic trees typically represent the evolutionary history of samples, where samples occur at the leaves of tree and internal nodes and edges/branches are created to connect the samples based on evolutionary relationships. In this patent, we use the term phylogenetic tree to refer this type of tree as well as the concept of creating transmission trees, in which patient samples are directly connected with edges (and internal nodes/branches are not created). Furthermore, we can also broaden the concept of phylogenetic tree or transmission tree to a phylogenetic graph or transmission graph, in which the relationship between samples is no longer represented by a tree (a graph in which there is exactly one path between samples). This phylogeny or transmission graph may include multiple edges or paths between samples, which may represent many possible ways of a transmission occurring and may have a probability or confidence score associated with the multiple edges/paths between samples. In certain embodiments a pathogen is a species of ESAKPE pathogen. In certain embodiments a transmission path of related pathogens is determined according to the transmission or correlate graph. In certain embodiments a parent pathogen or a patient zero is identified according to a transmission path. In some embodiments a probable location of a related pathogen is predicted according to the transmission path.

In certain embodiments, a transmission metric is generated using probabilistic methods that incorporate proximity information (e.g., proximity tag information, time and coordinate; e.g., three dimensional coordinate information), and pathogen tag information (e.g., genomic sequence data) to generate probable transmission links. In some embodiments, a transmission metric includes host response to a pathogen, pathogen growth/mutation rates, and environmental variables impacting growth/mutation rates (e.g., like disinfection effectiveness and ABX selection). In certain embodiments, a transmission metric is generated, in part, using a Bayesian inference scheme based on phylogenetic tree data (e.g., see Drummond and Rambout, *BEAST: Bayesian Evolutionary Analysis By Sampling Trees*. (2007) BMC Evol. Biol. 7:214; Didelot and Falush, *Interference Of Bacterial Microevolution Using Multilocus Sequence Data* (2007) Genetics 175(3):1251; Didelot, X. et al. *Bayesian Inference Of Infectious Disease Transmission From Whole-Genome Sequence Data* (2014) Mol. Biol. Evol. 31(7):1869-79; Cottam E. M., et al., *Transmission Pathways Of Foot-And-Mouth Disease Virus In The United Kingdom* (2007) PLoS Pathog. 4(4):e1000050; Jombart, T. et al., *Bayesian Reconstruction Of Disease Outbreaks By Combining Epidemiologic And Genomic Data* (2014) PLOS 10(1):e1003457.

In some embodiments a program herein is configured to instruct a microprocessor to obtain or retrieve one or more genomic sequence data files comprising genomic sequence data of one or more pathogens. In certain embodiments, a microprocessor is instructed to generate a pathogen tag for each pathogen where each pathogen tag comprises genomic sequence data related to the pathogen, a pathogen identifier, and a proximity tag comprising a location and/or object from where the pathogen was originally obtained (e.g., where the sample was obtained). In some embodiments a program herein is configured to construct a phylogenetic tree. In some embodiments a program herein is configured to construct a phylogenetic tree from one or more genomic sequence data files thereby determining a relationship between the genomic sequence data obtained from two or more pathogens. In certain embodiments, determining a relationship between the genomic sequence data obtained from two or more pathogens comprises comparing genomic sequence data and/or other information obtained from proximity tags and/or pathogen tags. For example, a pathogen tag often comprises a unique pathogen identifier and a proximity tag. The proximity tag often provides information as to when (period of time) and where (exact or probable coordinate) the sample comprising the pathogen (or nucleic acid of a pathogen) was isolated. The time period and coordinate information included in a proximity tag for a pathogen (pathogen tag) can be used to identify other related pathogens and to determine a phylogenetic relationship that identifies a relation between pathogens (i.e., related pathogens). Accordingly, in certain embodiments, genomic sequence data, as well as location and time can be used to determine a relationship between two or more pathogens. Further, in certain embodiments, a pathogen tag comprises a proximity tag which comprises health information of a patient infected with said pathogen. Non-limiting examples of health information includes health symptoms associated with an infection, as well as degree and intensity of the symptoms, vitals (e.g., temperature, blood pressure, heart rate, respiration), blood work data (e.g., blood cell counts, c-reactive protein, liver enzymes, etc.), other visual or blood indicators of the degree of an infection, and overall health of the infected subject. In some embodiments, health information comprises genotype and/or phenotype of a subject (e.g., an infected subject, a host). Such health information can be used to determine or estimate the virulence of a pathogen. Accordingly, in certain embodiments, two pathogens can be identified as related pathogens according to a similarity of symptoms, including degree, amount, duration or onset thereof, between two or more infected patients.

In some embodiments, methods and systems described herein incorporated some or all of the elements of a real time patient analytics system, a genomics processing framework (e.g., the framework described in Andry, F. et al., *PAPAyA: A Highly Scalable Cloud-Based Framework for Genomic Processing* (2016) Proceedings of the 9th International Joint Conference on Biomedical Engineering Systems and Technologies (BIOSTEC), vol. 3, Bioinformatics, 198-206, which is incorporated herein by reference in its entirety), Correlate algorithms in the real time patient analytics system, Data Mapping (including location distances) on premise, Pipeline algorithms in genomics processing framework for QA checking, MLST typing, Phylogeny tree building, and tree rendering/workflow support in the user interface.

In certain embodiments, a transmission metric comprises a probability distribution. In certain embodiments, implementation of the edge weighting and/or Random Walk techniques described herein provide a probability distribution representing a likelihood a source of an infection spread randomly or non-randomly. For example, one implementation of the Random Walk technique could provide a probability distribution representing the likelihood that an inspector looking for the source of an infection spread randomly moving on graph links will arrive at any particular node (patient or caregiver or location). In some embodiment, an algorithm works by counting the number and quality of links to a node to determine a rough estimate of how important that node is in the spread of corresponding infection. In other words, instead of providing a "transition path", an algorithm described herein can assign a probability value to each node (e.g., patient, caregiver, and/or location) to estimate the importance of each node was to the spread of a particular pathogen. In some embodiments, an algorithm described herein determines the most likely path for a pathogen being transmitted from each node to another, e.g. from a particular patient to another patient.

Systems, Machines, Storage Mediums and Interfaces

Certain processes and methods described herein often cannot be performed without a computer, microprocessor, software, module or other machine. Methods described herein typically are computer-implemented methods, and one or more portions of a method sometimes are performed by one or more processors (e.g., microprocessors), computers, or microprocessor controlled machines. Embodiments pertaining to methods described in this document generally are applicable to the same or related processes implemented by instructions in systems, machines and computer program products described herein. Embodiments pertaining to methods described in this document generally can be applicable to the same or related processes implemented by a non-transitory computer-readable storage medium with an executable program stored thereon, where the program instructs a microprocessor to perform the method, or a part thereof. The descriptive term "non-transitory" as used herein is expressly limiting and excludes transitory, propagating signals (e.g., transmission signals, electronic transmissions, waves (e.g., carrier waves)). The terms "non-transitory computer-readable media" and/or "non-transitory computer-readable medium" as used herein comprise all computer-readable mediums except for transitory, propagating signals. In some embodiments, processes and methods described herein are performed by automated methods. In some embodiments one or more steps and a method described herein is carried out by a microprocessor and/or computer, and/or carried out in conjunction with memory.

Machines, software and interfaces may be used to conduct methods described herein. Using machines, software and interfaces, a user may enter, request, query or determine options for using particular information, programs or processes (e.g., obtaining reads, recruiting reads, mapping reads, obtaining genomic sequence data, comparing genomic sequence data, triggering notifications or alerts, identifying related pathogens, providing pathogen tags, providing proximity tags, generating phylogenetic trees, generating transmission metrics or transmission paths, identifying patients, unencrypting or encrypting data (e.g., unique identifiers); accessing patient data, accessing confidential information; the like or a combination thereof), which can involve implementing statistical analysis algorithms, statistical significance algorithms, statistical error algorithms, statistical probability algorithms, iterative steps, validation algorithms, and graphical representations, for example. In some embodiments, a data file may be entered by a user as input information, a user may download one or more data files by a suitable hardware media (e.g., flash drive, etc.), and/or a user may send a data set from one system to another for subsequent processing and/or providing tags, phylogenetic trees, transmission metrics, sequence data (e.g., send sequence data from a sequencer to a computer system for sequence read mapping, pathogen identification, determining SNP differences, and the like).

A system typically comprises one or more machines. In certain embodiments, each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations.

Where a system includes two or more machines, some or all of the machines may be located at the same location as a user, some or all of the machines may be located at a location different than a user, all of the machines may be located at the same location as the user, and/or all of the machine may be located at one or more locations different than the user.

In some embodiments, a method or process is performed by multiple computing apparatus and a subset of the total processes performed by the system may be allocated to or divided among particular computing apparatus in the system. Subsets of the total number of processes can be divided among two or more computing apparatus, or groups thereof, in any suitable combination. A multi-computing apparatus system sometimes includes one or more suitable servers local to a sequencing apparatus, and sometimes includes one or more suitable servers not local to the sequencing apparatus (e.g., web servers, on-line servers, application servers, remote file servers, cloud servers (e.g., cloud environment, cloud computing)).

In some embodiments a user interacts with an apparatus (e.g., a computing apparatus, a sequencing apparatus). A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses (multiple apparatuses, also referred to herein in plural as apparatus), computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, cell phones, and the like. A computer system may comprise one or more input means such as a keyboard, touch screen, mouse, voice recognition or other means to allow the user to enter data into the system. A system may further comprise one or more outputs, including, but not limited to, a display (e.g., CRT, LED or LCD), speaker, FAX machine, printer, or other output useful for providing visual, auditory and/or hardcopy output of information (e.g., outcome and/or report).

A system can include a communications interface in some embodiments. A communications interface allows for transfer of software and data between a computer system and one or more external devices. Non-limiting examples of communications interfaces include a modem, a network interface (Ethernet/WiFi), a communication port (e.g., a USB port, HDMI port), Bluetooth, a PCMCIA slot and/or card, and the like. Data may be input by a suitable communication interface, device and/or method, including, but not limited to, manual input devices and/or direct data entry devices (DDEs).

A system may include software useful for performing a process described herein, and software can include one or more modules for performing such processes. The term "software" refers to computer-readable storage medium comprising program instructions (e.g., an executable program) that, when executed by a computer, perform computer operations. Instructions executable by the one or more microprocessors sometimes are provided as executable code, that when executed, can cause one or more microprocessors to implement a method described herein.

An exemplary system is shown in FIG. 1. Patient, pathogen (e.g., pathogen tags), object (e.g., proximity tags), samples and/or caregiver data can be generated, collected, and processed locally, for example in a hospital or caregiver facility 106, which data may include device data 121 that may include location and time information associated with an object. For example device data 121 may include patient location data assembled according to patient check-in time, check-out time, and patient location within the hospital or caregiver facility, (e.g., lobby, treatment room, etc.) and may include collection of data from a real time location system (RTLS). For example, an object (e.g., a patient, upon check-in), may be provided a radio frequency identification device (RFID) which can provide real time locations of a patient, caregiver, visitors or staff within a medical facility, which data is recorded, and assigned an appropriate identifier. Pathogen tags may also be generated from a laboratory input system 124 and/or directly from a DNA processor 126 (e.g., a sequencer, computer linked to a processor, a sequence database). Laboratory input systems 124 and DNA processors 126 can also provide MLST and SNP data for pathogens obtained from an object (e.g., patient, caregiver, device) and associate such information with a pathogen tag. Other input systems (e.g., 122, 123 and 125) may also generate proximity and pathogen tags and one or more of the input systems (e.g., 122-126) may be integrated into a device (e.g., 116). A computer-implemented system may include a local data aggregation system 107 and/or one or more remote data aggregation systems 113 which can encrypt, and decrypt, sensitive patient information and assign, encrypt, decrypt and re-assign patient identification information (e.g., ID numbers, names, birthdates, etc.) as well as regulate, deny and/or authorize access to some or all information in the system. Output information related to diagnosis and epidemiology 120, including phylogenetic trees, transmission metrics, sequence data, pathogen tags and proximity tags may be provided by means of a user interactive display 119 where data may be visualized, analyzed, edited, deleted, saved and/or submitted for further processing. Pathogen sequence information may be received, analyzed and processed by a genomics pipeline processing system (GPPS) 101, which can align and/or map nucleic acid sequences, assemble nucleic acid sequences, generate and compare genetic data (e.g., sequence data, MLST typing, SNP data), generate phylogenetic trees, and determine phylogenetic relationships among pathogens. A genomics pipeline processing system (GPPS) 101 can identify a set of related pathogens according to a phylogenetic relationships between a plurality of pathogens (e.g., pathogen tags), and provide a set of related pathogens (e.g., a set of related pathogen tags). Information sent to and from a genomics pipeline processing system may be processed by a data aggregation system 113. Data and information generated by a GPPS can be sent to a clinical decision support engine 105 for further processing where, e.g., phylogenetic relationships generated by a GPPS system, are processed into a transmission metric and exported by a data export system 104 back to a user interface (e.g., 119, 120) for analysis, and/or may be stored in a database 108 for later access. A clinical decision support engine 105 may receive instructions from a module (e.g., 110) which directs a processor to generate a transmission metric while applying novel edge weighting and transmission metric algorithms disclosed herein. Proximity tag information (e.g., including patient data, location and/or time information) associated with nodes of a transmission metric may be stored and accessed from an integrated storage media 111. Some or all information generated by or used by the system may be stored locally or remotely in one or more accessible databases (e.g., 109, 118).

Figure 16:
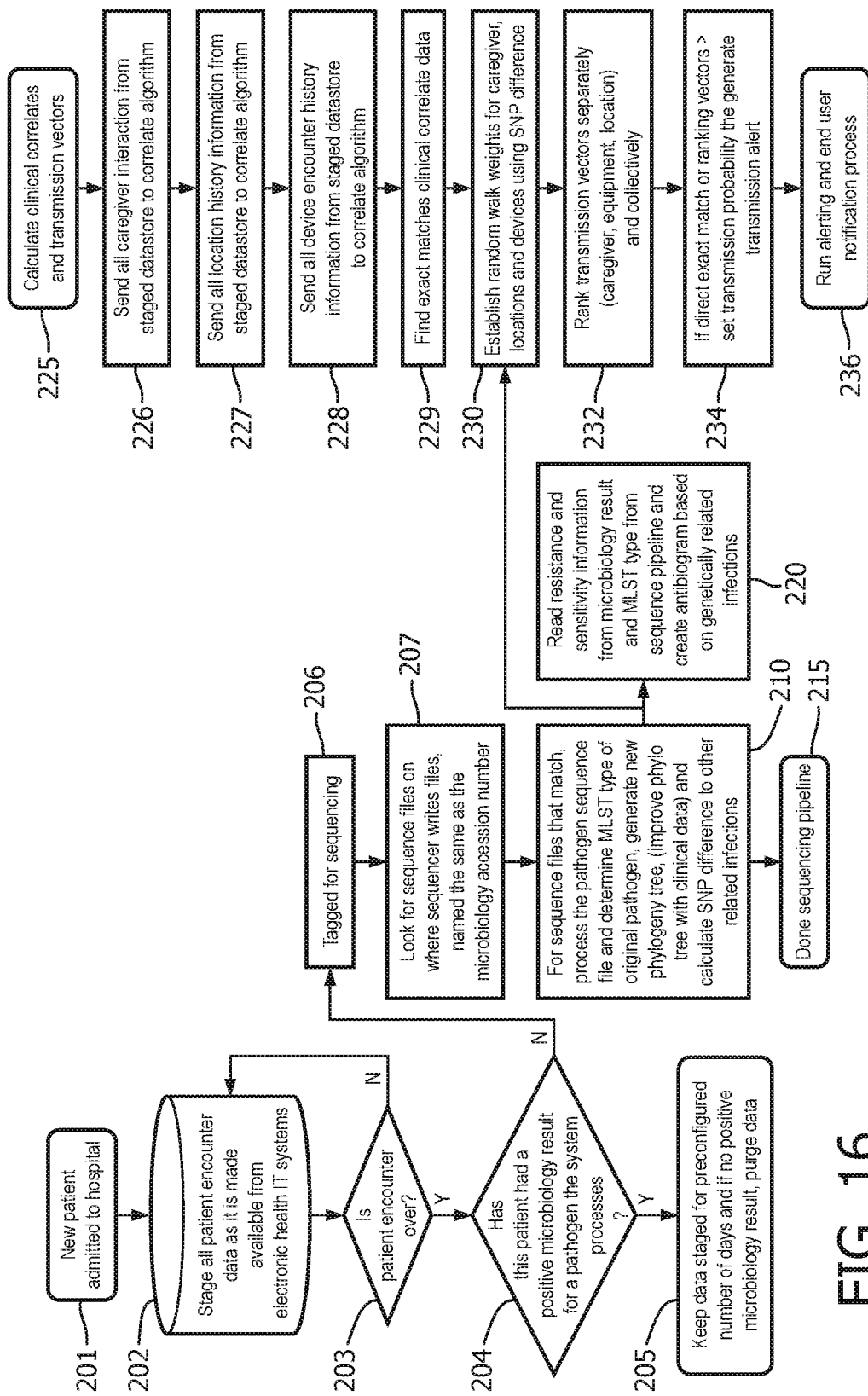
FIG. 16 shows a flow chart illustrating one embodiment of the process steps conducted by a system disclosed herein.

FIG. 16 shows a flow chart illustrating one embodiment of the process steps conducted by a system disclosed herein. Patient data is input, staged, stored, processed and made available by an electronic health IT system 202 initiated upon admitting a new patient to a hospital 201. Patient encounter data continues to be processed and staged until the system is cued that the patient encounter is over by a system query 203. After termination of a patient encounter, the system is queried to determined if a sample was generated 204. For example a system may ask if a patient sample was obtained and if the sample was positive or negative for the presence of a microorganism (e.g., a pathogen). If a sample is determined to be negative for the presence of a microorganism or pathogen, patient encounter data is often moved to storage 205. If a positive result is determined, a microbiologic sample is sent to be sequenced 206 to obtain sequence information from the pathogen. Sequence information for the pathogen is obtained by the system 207, which information is used to generate a pathogen tag. Pathogen sequence information is then processed and compared 210 in an attempt to identify and/or characterize the pathogen in the sample. Related pathogens may be identified upon comparison of sequencing information, MLST typing data and SNPs to a database containing sequence information from other pathogens. If a subset of related pathogens is identified, a phylogenic tree can be generated. Data obtained from the comparison of 210 can be used to generate an antibiogram 220.

An antibiogram (e.g., a hospital antibiogram) is, generally, a periodic summary of antimicrobial susceptibilities of local bacterial isolates submitted to a clinical microbiology laboratory (e.g., a hospital's clinical microbiology laboratory). Antibiograms are often used by clinicians to assess local susceptibility rates, as an aid in selecting empiric antimicrobial therapy, and in monitoring resistance trends over time within an institution. Antibiograms can also be used to compare susceptibility rates across institutions and track resistance trends. Keeping track of this information is important to monitor emerging trends in antimicrobial resistance and support clinical decision making, infection-control strategies, and resistance containment strategies.

In certain embodiments, the present invention comprises creating antibiograms using genomic subtype information.

In certain embodiments, antibiograms are generated as described in International Patent Application No. PCT/IB2016/051352, filed Mar. 10, 2016 (Publication No. WO2016/142890) which is incorporated herein by reference in its entirety. In some embodiments, the present invention utilizes molecular epidemiology and next-generation sequencing technologies (NGS) to monitor multi-drug resistant pathogens, determine their antimicrobial resistance, provide early insight into emergent microbial threats, and recommend antimicrobial treatments.

In some embodiments, pathogens and other microbes of interest are cultured and tested for sensitivity (or conversely, resistance) to various antimicrobials. The cultured pathogens are sequenced (e.g., by whole genome sequencing, targeted sequencing, etc.) and their genomic data (e.g., a Fasta sequence file) is often compared against a publicly-accessible or private database of genomic data to identify the particular subtype of the tested pathogens. In some embodiments, the sensitivity/resistance data according to subtype is then presented to a user.

In certain embodiments, a computer processor is configured to receive information concerning the sensitivity of a pathogen isolate to at least one antimicrobial (e.g., antibiotic, anti-viral); to receive information concerning the strain or subtype of the pathogen isolate; and provide an output (e.g., a graphical or visual display) indicating the sensitivity of a pathogen isolate, or group of related pathogens to an antimicrobial treatment. Computer-implemented methods of determining the sensitivity of a pathogen to a treatment (e.g., as based on genomic sequence data) and identifying strains or sub-types of related pathogens based on treatment sensitivities is described in International Patent Application No. PCT/IB2016/051352, which is incorporated herein by reference in its entirety. In one embodiment, receiving information concerning a subtype of a pathogen isolate comprises receiving data describing at least part of the genome of the at least one isolate; comparing the received genomic data from the sequencing operation against a reference database; and identifying a matching subtype for the at least one isolate from the results of the comparison (e.g., see PCT/IB2016/051352).

Figure 11A:
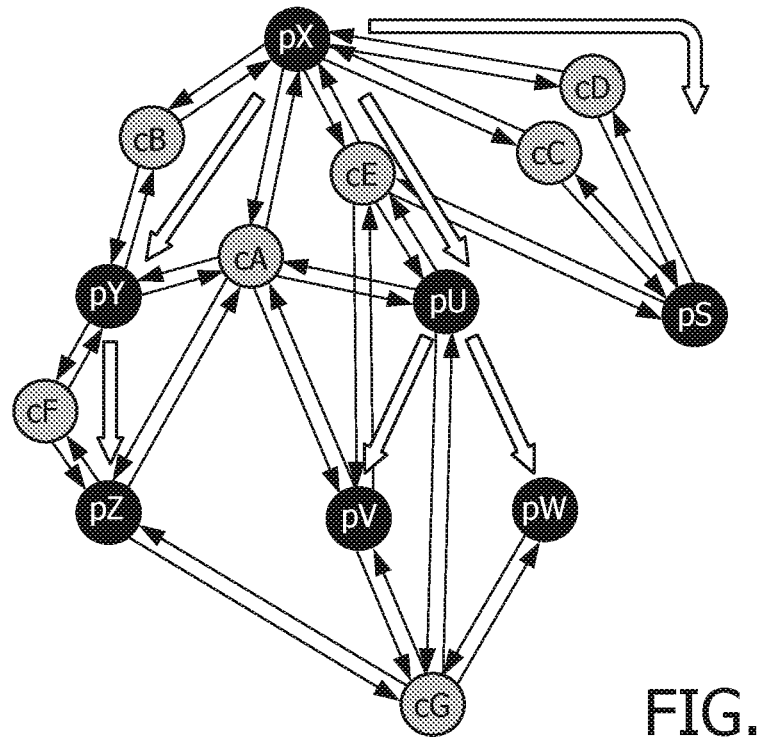
Figure 11B:
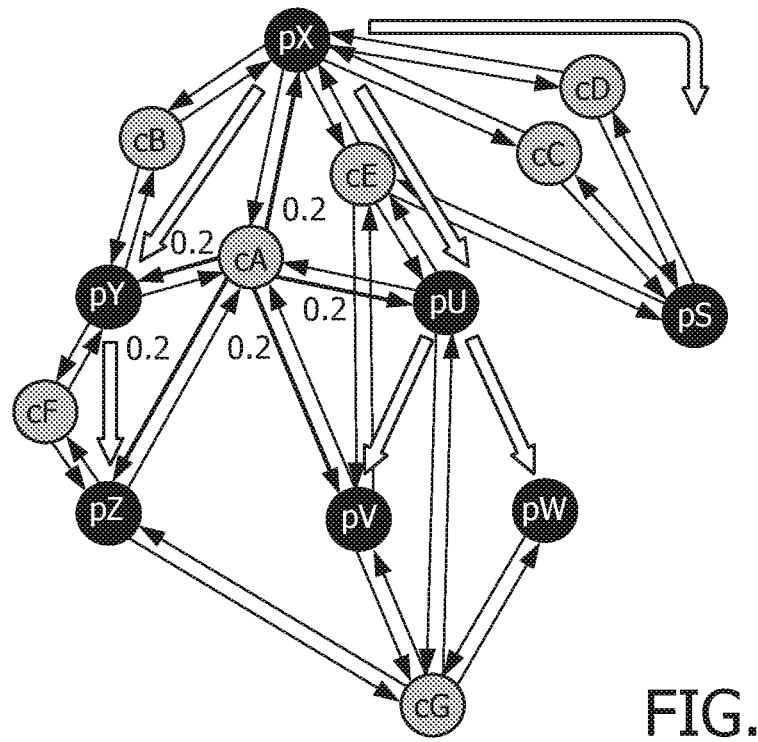
Figure 14A:
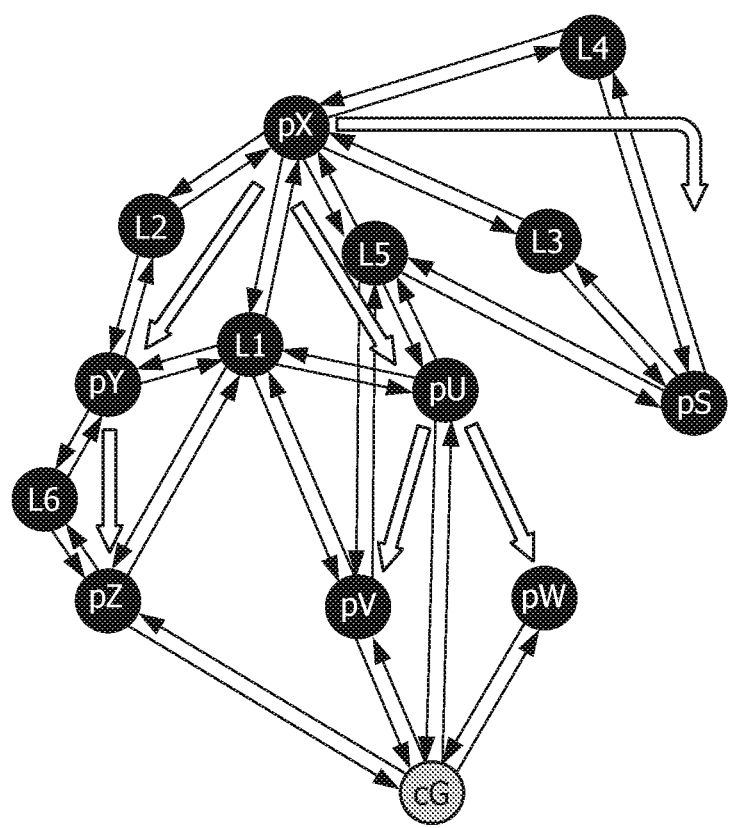
FIG. 14A shows an embodiment of a transmission metric comprising location nodes L1 to L7 (e.g., each representing a proximity tag for an object) and patient nodes (e.g., each comprising a pathogen tag).

Proximity tag and/or pathogen tag correlates 225 from, for example, caregiver interactions 226, location history information 227 and device encounters 228, can be accessed from a storage medium and processed to determine exact matches from clinical correlate data 229. Random walk weights for caregivers, locations and devices can be determined using SNP differences 230 (e.g., by a process outlined in FIGS. 11-12). Node ranks can then be determined 232, (e.g., by a process outlined in FIGS. 13 and 14). If direct exact match or high probability ranking vectors are determined, transmission probabilities can be determined and a transmission alert can be generated 234/236.

A module described herein can exist as software, and/or instructions (e.g., processes, routines, subroutines) embodied in the software that can be implemented or performed by a microprocessor. For example, a module can be a part of a program that performs a particular process or task. The term "module" refers to a self-contained functional unit that can be used in a larger machine or software system. A module can comprise a set of instructions for carrying out a function of the module by one or more microprocessors. Instructions of a module can be implemented in a computing environment by use of a suitable programming language, suitable software, and/or code written in a suitable language (e.g., a computer programming language known in the art) and/or operating system, non-limiting examples of which include UNIX, Linux, oracle, windows, Ubuntu, ActionScript, C, C++, C#, Haskell, Java, JavaScript, Objective-C, Perl, Python, Ruby, Smalltalk, SQL, Visual Basic, COBOL, Fortran, UML, HTML (e.g., with PHP), PGP, G, R, S, the like or combinations thereof.

A computer program product or module, or collection of modules is sometimes embodied on a non-transitory computer-readable medium, and sometimes is tangibly embodied on a non-transitory computer-readable medium. In certain embodiments a computer-readable storage medium comprises an executable program stored thereon. A module sometimes is stored on a non-transitory computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

EXAMPLES

The examples set forth below illustrate certain embodiments and do not limit the technology.

Example 1

An embodiment of the system can be hosted on networked computing platform (e.g., FIG. 1, 103) and includes a plurality of complementary analytics systems including a genomics pipeline processing system (GPPS) 101, and a real time patient analytics system (PAS). In some embodiments, a main system is hosted in a cloud-based infrastructure and comprises of the genomics processing framework 101, a genomics pipeline processing system, and the real time patient analytics system. In certain embodiments, an edge device stages all electronic clinical information and is triggered by a positive culture for a pathogen and source of interest. Once triggered, the edge device automatically starts to move staged through a de-identification processor 107 where it removes all PHI and site identifiable information prior to sending over a secure encrypted connection to the analytics cloud 103. Once there the system detects the application trigger, and new data for the person who as referenced in the microbiology result, that data is also sent to the cloud with the appropriate GUIDs encoded. Other triggers can be based on signs of infection from analysis of the clinical information, and risk of the subject based on historical clinical phenotypical or genomic data.

An onsite user, once authenticated locally, is provided access to the application where he can match what was or is loaded into the NGS sequencer (by file name) to the microbiology generated positive culture. This matching pre-assumes the accession number is in the sequencer file output, and a matching method is used to create a unique file name which is a series of globally unique IDs (GUID) relating the cloud data patient ID, Accession number, and other site information such as sequencer used and its settings.

Once the sequence file is written by the NGS sequencer, the edge device copies the file, renames it using the required GUIDs, and transports the file from the premise to the cloud via a secure, FTP service. Once in the cloud, the real time patient analytics system initiates the genomics processing framework or GPPS pipeline appropriate for the type of sample presented. In certain embodiments, the matching of the sequence ID and clinical meta data to a sample is maintained by a GUID linked to the accession for a culture and specific pathogen reported through that microbiologic message. In some embodiments, direct sample sequencing is supported with metagenomics to identify a probable pathogen list, probability of illness resulting from each suggested ABX susceptibility and risk based on where a pathogen caries resistance genes (chromosomal or plasmid). The file name may contain references to the type of sequence file it contains, such as which pathogen, or what type of oncological sample is contained.

In certain embodiments, the presence of a pathogen in a sample is determined. In certain embodiments, upon identification of a pathogen, a pathogen tag is generated indicating at least the source of the pathogen (e.g., sample), time of sample retrieval, and/or coordinate of the sample source. In some embodiments, the pathogen tag is associated with one or more proximity tags indicating contact of the pathogen with one or more objects. In certain embodiments a system comprises a workflow trigger that can initiate a notification upon identification of a pathogen. In some instances the identification of a pathogen and/or the creation of a pathogen tag triggers a notification which can initiate a search and/or retrieval of all historical proximity tags and/or other pathogen tags having a relationship to the pathogen tag created. In some embodiments, a workflow of a system described herein comprises instructions to search for, identify, expose, and/or retrieve historic proximity tags in response to a notification indicating the presence of a pathogen. Relationships of tags can be identified according to probabilistic correlations, probabilities of contact and/or probabilities of proximity overlap. In certain embodiments, such relationships are provided by a transmission metric which is generated in response to a workflow trigger from a notification of a positive culture (e.g., the presence of a pathogen).

genomics processing framework or GPPS starts the processing and returns the process ID which the real time patient analytics system should monitor to verify the pipeline execution completes, retrieve the quality verifications at each step of the pipeline, and what results are provided by the genomics processing routines. The real time patient analytics system receives status and intermediate output result as the pipeline executes and updates a user interface with the process status and QC results until the pipeline completes.

Once the pipeline completes for all species samples (pathogens, or host centric, or oncological sample), a phylogeny tree is created. Clinical data such as hospitalization and care contact dates, drug resistance (in the case of pathogen), tumour growth rate, and other phenotypic or syndromic clinical data, or environmental information that can impact pathogen/tumor growth and mutation rates, is inputted to the phylogenetic tree methods so it can disambiguate parent child relationships.

Tree rendering is based on either absolute or fuzzy single nucleotide variants, or SNP counts to determine genetically similar infections.

Phylogeny or transmission tree information comprises nodes IDs so all resulting genomic data and clinical data can be linked back to the actual pathogen that was sequenced. Parent child relationships and SNP count are used to derive exact match and probabilistic correlates. These correlates are related to what was found to be in common to the locations, caregivers, procedures and devices the patient had come in contact with. The correlates are based on the care data extracted from the electronic sources including clinical findings and assessments, procedures (operative or investigative), interventions notes. With every data sent to the cloud, a location is assigned based on look-up tales configured on the on-prem edge device. User associations are based on electronic signatures associated with the charting of the clinical data and, a location of where the interaction is based on a location label transformed to a 3 dimensional location within the facility.

By using coordinate based location and not just label based, the correlate methods can look not only for exact location matches but proximally close matches in the case where adjacent room numbers are not proximal to each other or specific care environments share common HVAC service.

Exact matches for correlates are identified by color coded connectors along the Phylogeny tree and a probability of correlates are shown based on the entire tree or user selected limbs or exact nodes. Non-exact match correlate probability data and ranking can be done through a multitude of techniques.

The preferred embodiment includes an antibiogram based on Microbiology interfaced susceptibility data fused with MLST typing as a method of risk stratification of certain infections, as well as recognizing gene expression signatures in the sequence that indicate with a trending toward antibiotic resistance or an actual conversion of the strain to either single drug resistance or multiple drug resistance.

The preferred embodiment include cloud based decision rules that provide the infection control or sequencing process owner insights to the data. Typical notification and evidentiary data include but are not limited to:

"New previously unknown MLST type strain encountered" (node in phylogeny tree)
"Positive ESKAPE culture found from an expected sterile source" (accession number(s))
"Positive ESKAPE culture found from an expected sterile source not seen in sequence list" (accession number(s))
"Rate of positive cultures for [Pathogen] seen from [source] exceeds historical trends" (Pathogen epicurve)
"Possible new transmission event detected" (Nodes in phylo tree with low SNP count and exact match correlate or probability correlate >xx %)
"New Correlates found for existing transmissions outbreaks" (Pathogen, nodes, correlates)
"New single drug resistance discovered for [MLST type]" (tree, node)
"New multi-drug resistance discovered for [MLST type]" (tree, node)
"Resistance gene found on plasmid for (accession number(s))"
"Patient receiving antibiotic with low effectiveness"

By using coordinate based location and not just label based, the correlate methods can look not only for exact location matches but proximally close matches in the case where adjacent room numbers are not proximal to each other.

Exact matches for correlates are identified by color-coded connectors, node or connector pulsing using animations, or other methods to draw the user's attention to parts of the phylogeny tree where correlates are highly suggestive to transmissions. This initially is disclose to the user for the nodes in focus based on the current time window as defined in the epi-curve navigator. The user is allowed to change the time range defined by the epi-curve navigator and is also allowed to select limbs or exact nodes thus retriggering the correlate methods to recalculate the nodes in focus. Non-exact match correlate probability data and ranking can be done through a multitude of techniques.

In some embodiments, patient, device and caregiver movement through the system can be animated for adjacent low SNP difference infections to visualize the high probability contact points to aid the human observer to target high plausible transmissions suggested by the non exact match transmissions.

The preferred embodiment includes a Random Walk or Markov Chains with un-weighted (i.e. uniform weighting), and weighting based on SNP count (genomic information) for binary match correlates (caregiver and devices either match or do not), and proximity matching (location matching can be exact, close or far). Alternative embodiments include exhaustive pair wise evaluation (as all nodes in the community) and parent child evaluation (tree rendered relationships only).

Using the Random Walk approach described herein, we can further refine the embodiment associated with addressing exact and non-exact matches across the patient history and allowing an independent assessment independent of the phylogeny tree parent and child relationships.

(Note: unless otherwise stated the match analysis can apply to any of the binary correlates, caregiver, environmental/device or location).

Figure 7A:
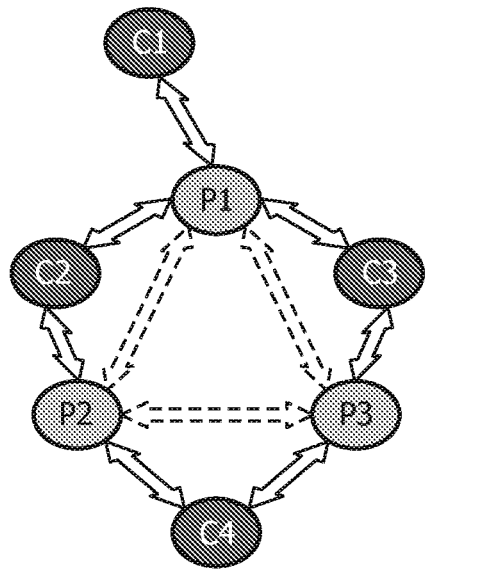
FIGS. 7a and 7b show an embodiment of a transmission metric (correlate graph) of a subset of related proximity tags represented by nodes (circles) and edges (arrows). Nodes P1, P2 and P3 represent proximity tags for patients P1, P2 and P3, which, in some embodiments, can be associated with pathogen tags which can be used to determine transmission edges. Nodes C1-C4 represent proximity tags for caregivers C1-C4. Transmission edges can comprise a probability of transmission defined in part by information derived from a phylogenetic tree (e.g., relatedness of pathogens, e.g., FIG. 7a), and proximity tag overlap (i.e., probable intersects, e.g., intersects of a time period and intersects of object coordinates). In this embodiment, links (i.e., edges) are bi-directional and may or may not be equally weighted. If equally weighted, the edges of FIG. 7 are created by analyzing the caregiver, transactions extracted from the clinical and EHR interfaces documenting the care process, and do not take into account any genomic sequence data, coordinate data or time data. Alternatively, the edges may have different weights where calculating the weights may be based on genetic variations and mutational differences, such as SNPs.
Figure 7B:
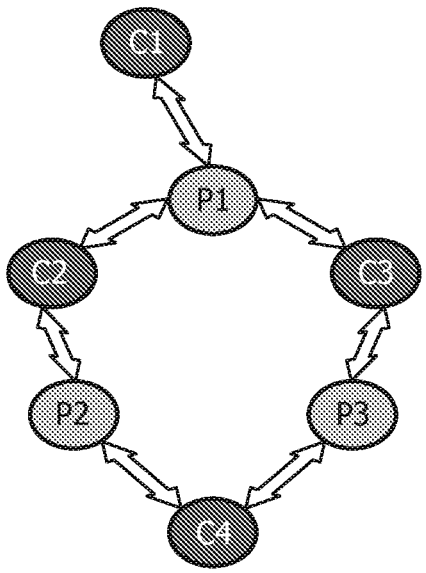
Figure 8:
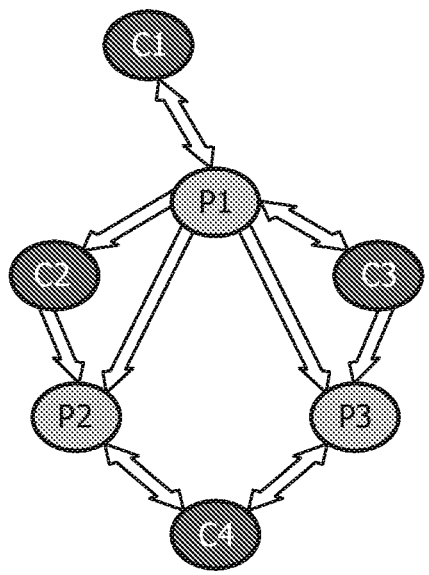
FIG. 8 shows an embodiment of a transmission metric of a subset of related proximity tags represented by nodes (circles) and edges (arrows). Nodes P1, P2 and P3 represent proximity tags for patients P1, P2 and P3. Nodes C1-C4 represent proximity tags for caregivers C1-C4. Edges from P1 to P2, and from P1 to P3, are unidirectional and provide a high confidence in the direction of transmission defined, in part, by the phylogenetic tree data derived from genomic sequence data.

FIGS. 7 (7a & 7b), and FIG. 8 describes inclusion, direction and equal weighting to the potential paths describing the patient transmissions across the caregiver correlates for three sample patients. Note the links are bi-directional and equally weighted, and in the case of FIG. 7 do not take into account any genomic information what-so-ever. This approach is used when there is low confidence in the phylogenetic tree parent to child associations resulting from:
1. Very low SNP variation across the 3 pathogen/patient representations and poor accounting of the chronological fiduciary points.
2. Cases which seem to be discovered at the same time with all patients care encounter occurring at the same time.
3. When there is poor access to high fidelity electronic correlate data.

In some embodiments, a phylogenetic tree is rendered as a blob of nodes rather than exact but incorrect sequencing of parents and children. In this embodiment, the app is communicating that these are very similar infections without exact matches available to the system.

In FIG. 8, we have high confidence in the transmissions defined by the phylogenetic tree (i.e. the infection from patient 1 was transmitted to patient 2 and 3). In this case we enforce unidirectional links from P1 to P2 and P3 and the common caregivers are modelled as unidirectional links. Note the correlates that are not shared are still assumed to be bidirectional, and in this case equally weighted. This approach is applied when:
1. There is low SNP variation between transmissions and,
2. There are either high fidelity accounting of the correlate data (e.g., Real Time Location System (RTLS)), and/or
3. The encounters are temporarily and chronologically separate.

For non-binary correlates where there can be exact matches or the matches can be expressed with regards to proximity with a discrete or continuous function. We can create the location distance matrix created by mapping in 3 dimensions all patient locations referenced to a common reference point (for example, the main entrance, emergency department entrance, helicopter pad, etc.). The distance can be used as an absolute distance for weighting or mapped to a non-continuous or non-parametric scale (for example, close and far).

In FIG. 10, we see an exact location match for each patient transmission below. We see several other locations that do not match across the patient stays. We use the location distance matrix previously described to infer a degree of closeness of 2 locations across patients. A degree of closeness can be discrete or continuous, or non-parametric. For example patient 1 and 2 shared location 2 during the stay but patient 1 also was encountered in location 3 and 5 while patient 2 was in location 4 and 6. If location 3 and 4 are next to each other in 3 dimensional space, there is a higher probability the patient transmission may have occurs there due to a shared infrastructure such as an HVAC (air handling) component, or maybe even a common service provider not represented in the electronic data feeds, like the food delivery service or housekeeping.

We also see location 5 and 6 are linked in this figure but based on the distance matrix, these are far apart and would either not be connected or would be weighted low for the method. Directionality of the paths are previously described.

Additional link weighting embodiments include accounting for pathogen and sample source for the sequence information as a way of knowing where the infection is, and its likely transmission method (direct contact, airborne, surface contamination . . . ). For example, a respiratory infection that can be spread by air would require close proximity for the transmission. In this case the method would not weigh distant locations or even allow them in the correlate calculation.

In some embodiments, a determination of transmission is based on direct physical contact between a subject and a pathogen source.

Example 2

In one embodiment, the pathogen is one identified in the Centers for Disease Control (CDC) mandated reporting of ESKAPE group and the setting is in the hospital, however this invention can be applied to community biomes, environmental monitoring for agriculture and livestock infections, and aide in early alerting for infections in a general the bio-surveillance. In some embodiments, data is gathered from a non-hospital bio surveillance case where correlate data is obtained from subject digital footprint of travel and location.

This invention solves several significant problems:
1) User experience that indicates the status of cloud based pipeline processing of genomic information related to pathogens.
2) User experience that indicates exact matching of correlates for specific parent and child nodes in a phylogeny tree.
3) User experience that indicates the most likely matching correlates based on a probabilistic matching of the transmission vector.
4) Weighting of the probabilistic transmission vectors based on the genetically determined similarity of infections (based on SNP differences, for example)
5) Automatically and systematically identify transmission vectors across defined systems (hospital, field, community . . . ).

The main elements of the solution, according to embodiments of the present invention, are PAS, GPPS, Correlate methods in PAS, Data Mapping (including location distances) on premise, Pipeline methods in GPPS for QA checking, MLST typing, Phylogeny tree building, and tree rendering/workflow support in the user interface.

Example 3

Figure 9A:
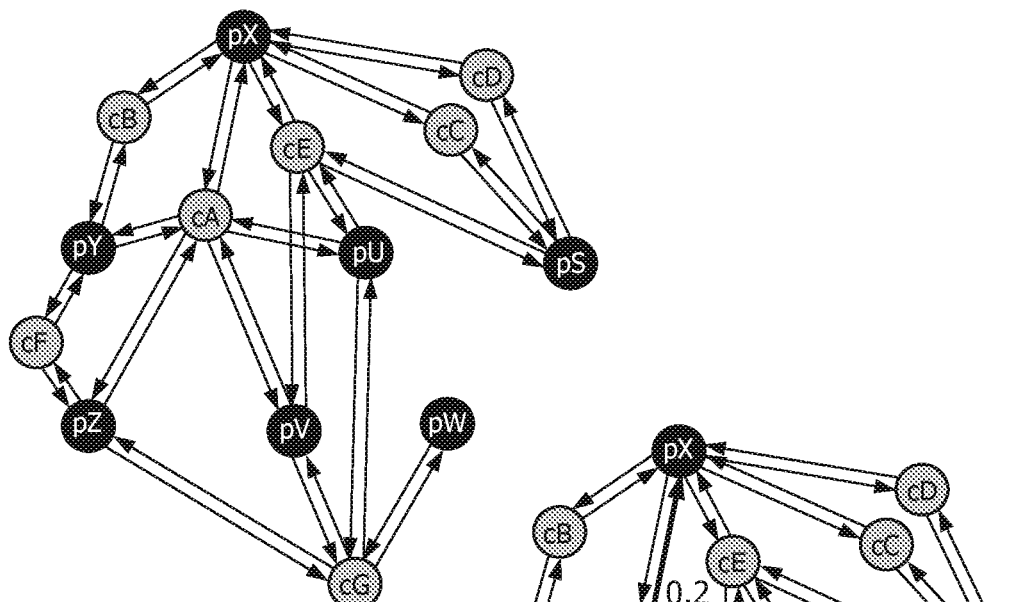
FIGS. 9A, 9B and 9C show examples of a transmission metric that includes embodiments of a process comprising a weighting scheme. Patients nodes are indicated by p (e.g., pS, pU, pV pW, pX, pY, and pZ) and caregivers nodes are indicated by c (e.g., cA, cB, cC, cD, cE, cF and cG).
Figure 9B:
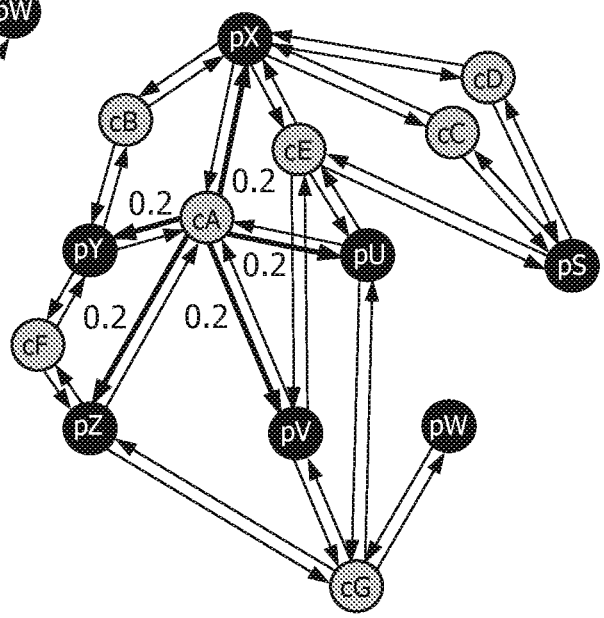
Figure 9C:
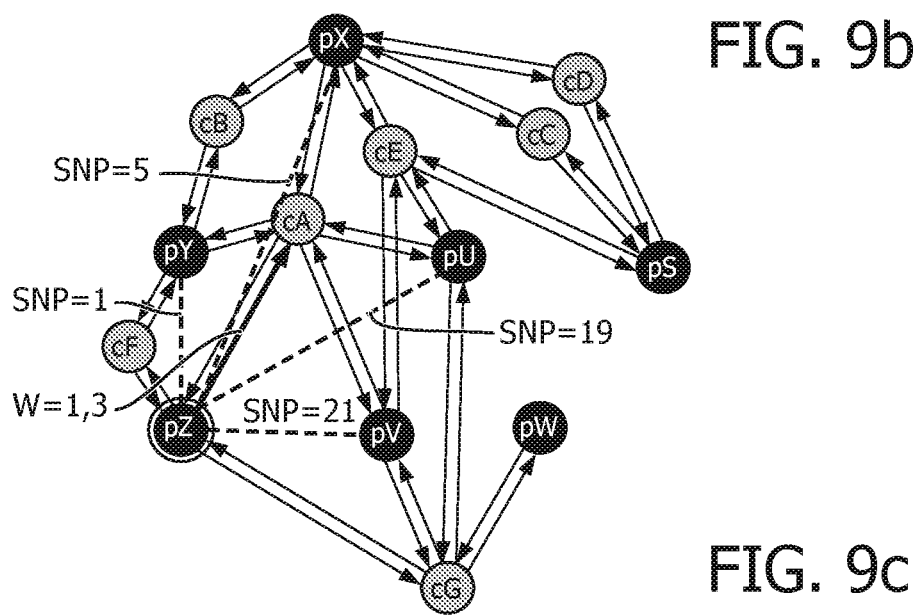

FIGS. 9a-c shows examples of a transmission metric that includes embodiments of a process comprising a weighting scheme. Other alternative weighting schemes may also be used to weight edges. FIGS. 9a, 9b and 9c includes patients nodes p (pS, pU, pV pW, pX, pY, and pZ) and caregivers nodes c (cA, cB, cC, cD, cE, cF and cG). In this embodiment, edges are only shown between patient and caregivers. Edges are provided weights, and the sum of all outgoing edge weights for each and every node is 1. The weighting scheme used pairwise SNP difference values. The process included: Step 1—weighting is assign uniformly to all outgoing edges for each caregiver node, (i.e. a caregiver is equally likely to receive pathogen from any patient that a caregiver makes contact with). Step 2—For each outgoing edge of a patient node to a caregiver, find all patients (other than the corresponding patient) connected to this caregiver. Step 3. For every such patient connection, add the weight as inverse of SNP difference between these two patients.

To protect against divide by 0, SNP difference of 0 are replaced with a default small non-zero value For missing SNP difference values, a default large value is used, e.g. 10 times the maximum SNP difference between samples FIG. 9c is an example for calculating the weight for the edge going from Pz to cA. Using the example SNP difference values, this weight would be $w=1/21+1/1+1/5+1/19=1.3$ Step 4. Normalize, so all outgoing weights for each node add up to 1. In this example this will change the w to 0.53.

The graph can potentially include "location" information (proximity information). One way to achieve this would be Add each location as a node to the graph Edges between patients and related location nodes Edges between every pair of location nodes Weight location-location edges based on their distance One weighing scheme for location node could be as follows with the understanding that other schemes may also be applied.

Outgoing edge weighting for each patient node, one of the following

Uniform: patient is equally likely to receive pathogen from any location in contact with Use SNP differences similar to the graph with patients and caregiver nodes For outgoing edges of a location node, equal total weight for going to patients or other locations For each outgoing edge of a location node to a patient: uniform weighting For each outgoing edge of a location node to another location, the weight is inverse of distance between these two nodes To protect against divide by 0, replace distance of 0 with a small value, e.g. 1/10th of minimum non-zero distance For missing distance values, use a large value, e.g. 10 times the maximum existing distance For a graph which includes patient nodes, caregiver nodes, and location nodes, the patient-caregiver and patient-location weighting schemes may be used in series to weight the edges using both the location distance and SNP difference values.

Example 4

In certain embodiments genomic sequence data comprises a sequence of one or more single nucleotide variants (SNVs) or single nucleotide polymorphisms (SNPs) that can be compared to a known reference genome or an entire genome sequence of a pathogen which can be constructed by either aligning sequence reads to a known reference genome, using genome assembly techniques, or a hybrid approach. When multiple pathogens have been sequenced the genome sequences from the samples can be compared to count the number of SNV differences between the genomes of two pathogens. In one embodiment, a genomic similarity can be measured by examining all known single nucleotide variants (SNVs) of a pathogen genome. In other embodiments genomic similarity is determined by only considering SNPs (which are SNVs that occur in at least two samples). Furthermore, genomic similarity can be measured more broadly by also considering other mutational differences, including but not limited to, insertions, deletions, inversions, rearrangements, tandem repeats, and copy number variations between samples. By examining these mutational differences a metric can be defined to measure the differences between samples. In one embodiment, a mutational difference score may simply be the number of SNV differences between two samples. In other embodiments, a difference score can be calculated based on a weighted sum of the differences observed between samples in the categories of mutational differences mentioned above. In certain embodiments related pathogens of a set are identified according to a correlation between a defined mutational difference score and a mutation rate (e.g., a period of time elapsed between pathogen isolation). In some aspects related pathogens of the set are identified according to a correlation between one or more mutational difference scores and an expected mutation rate. In some embodiments related pathogens of a set are identified according to a correlation between one or more mutational difference scores and one or more locations (e.g., locations associated with proximity tags). In certain embodiments related pathogens are identified by a process comprising a Random Walk or weighted Markov Chains. In certain embodiments, the random walk is used to provide a probability score for a correlate as being responsible for one or more transmissions, and correlates can be ranked according to the probability score. In certain embodiments the probabilistic correlations comprise probabilistic matches between of the probable coordinates of two or more proximity tags and the probable coordinates of one or more of the related pathogen tags. In certain embodiments determining the presence of one or more relationships in (d) comprises determining one or more temporal relationships between one or more human subjects and one or more related pathogens. In certain embodiments the temporal relationships comprise one or more probable intersects between two or more proximity tags. In certain embodiments a coordinate is within one or more defined regions which comprise one or more hospitals. In certain embodiments identifying a set of related pathogens comprises identifying one or more of the set of related pathogens to a sub-species level or strain level according to the genomic sequence data. In some embodiments identifying the set of related pathogens comprises a typing scheme, such as MultiLocus Sequence Typing (MLST), ribosomal MLST (rMLST), core genome MLST (cgMLST) and whole genome MLST (wgMLST), or identification of gene expression signatures, determining a pathogen's closest neighbor, determining a pathogen's mutation rate, determining pathogen growth rates, determining a pathogen's evolutionary distance between two or more other pathogens and/or generating a phylogenetic tree. In the literature, phylogenetic trees typically represent the evolutionary history of samples, where samples occur at the leaves of tree and internal nodes and edges/branches are created to connect the samples based on evolutionary relationships. In this patent, we use the term phylogenetic tree to refer this type of tree as well as the concept of creating transmission trees, in which patient samples are directly connected with edges (and internal nodes/branches are not created). Furthermore, we can also broaden the concept of phylogenetic tree or transmission tree to a phylogenetic graph or transmission graph, in which the relationship between samples is no longer represented by a tree (a graph in which there is exactly one path between samples). This phylogeny or transmission graph may include multiple edges or paths between samples, which may represent many possible ways of a transmission occurring and may have a probability or confidence score associated with the multiple edges/paths between samples. In certain embodiments a pathogen is a species of ESAKPE pathogen. In certain embodiments a transmission path of related pathogens is determined according to the transmission or correlate graph. In certain embodiments a parent pathogen or a patient zero is identified according to a transmission path. In some embodiments a probable location of a related pathogen is predicted according to the transmission path.

In some embodiments, a local reference genome for a pathogen species is obtained from a source (e.g., hospital) to better represent a local biome. In some embodiments, additional reference to a host health and/or host immune response is used to back fill when the actual transmission occurred based on pathogen incubation rate and host response.

Example 5—an Embodiment of Determining Related Organisms

A plurality of samples derived from patients, caregivers and devices are obtained and microorganism cultures from each sample are generated. Microorganism isolates are obtained and the genomic DNA of each organism isolate is sequenced. The sequencing can be performed using various sequencing technologies, e.g., next-generation sequencing technology such as Illumine HiSeq or MiSeq, or Pacific Biosciences. Sequence information obtained from full genome sequencing or targeted sequencing of each organism can be used.

The sequencing data is processed and compared to one or more reference sequences for the sequenced organism. An appropriate reference sequence can be identified using, e.g., prior knowledge, selective culture medium, any suitable microbiological evaluation and/or MLST typing. Once a reference sequence is chosen, the sequenced data can be aligned to the reference sequence using well-known methods such as BWA, Bowtie, etc., and differences between the sequenced data and the reference sequence can be identified using a suitable method to call variants (e.g., Samtools, GATK, or the like). Variations in a genome may be annotated to determine which mutations occur within important genes or in less important regions of a genome.

Pairwise distances between each pair of sequenced samples is calculated using, e.g., the R statistical modeling language and an R package such as APE which is used to form a distance matrix. A distance matrix can be based on the absolute number of differences or based on a probabilistic model, such as Jukes-Cantor. The distance matrix may then be used for building a phylogenic tree of sequenced samples and identifying any closely-related microorganisms from each of the sequenced samples.

An expected range of genetic changes (e.g., SNVs) over time for a transmitted infection is determined. One procedure for determining an expected range of changes over time involves examining neighbors that the phylogenic tree indicates are closely related, i.e., those neighbors which only have a limited number of changes between them (e.g. 10 SNPs) and are believed to be evolutionarily related, and measuring the range of changes between their genomes and dividing by the time between the isolation of their originating infections. Linear regression may also be used on the sample data to determine the average range of changes per unit time. Alternative procedures for determining the expected range of changes over time could include utilizing a controlled method, such as taking samples from the same patient over known period(s) of time and measuring the observed changes, using previously-determined information from third party sources or publications, or determining the expected range of changes from a plurality of samples taken from a known hospital-acquired infection. Other methods can be used to compute prediction intervals on the range of changes expected to be seen over time, and these intervals can be used to bound the typical range of expected changes.

For at least one pathogen sample, the number of mutational changes over time between that sample and at least one other pathogen sample is computed, and it is determined if the number of changes over time between those sample pairs is within or without an interval of the expected range of changes.

Pairwise distances between each pair of samples may be computed based on the number of SNP differences between the samples. The number of mutational changes may also be determined by counting, e.g., indels (insertions and deletions), genomic rearrangements (inversions and translocations), copy number changes, the absence or presence of genes, or some combination of the preceding features, and these changes may be measured in the full genome of an organism or part of the genome, such as the organism's chromosomes or plasmid.

Once pairwise distances have been calculated, each sample may be compared with every other sample to determine if the number of differences between the pair of samples falls within the expected range of differences we would expect to see from a transmitted infection given the time difference between the samples. The computed number of mutational changes between the samples may be normalized using the total number of genomic positions for which both samples have a base call, thereby reducing errors and noise arising in the physical transduction in the sample sequencing process.

For each pair of samples where the computed number of changes over time is within an interval of the expected range of changes, the associated pair of samples are marked as a potentially-transmitted infection. For example, if the number of changes is within some prediction interval, e.g., 95%, of the number of changes that are expected based on previous data, the sample would be marked as a potentially-transmitted infection.

A method to identify a transmitted infection may comprise determining which of the infection samples are from the same outbreak. This can be accomplished by conducting a breadth first search on a graph where each patient is a node and there is an edge between two nodes if the foregoing steps determine there likely was a transmission between the patients. Such a search essentially identifies patients within the same outbreak by starting with one patient and noting the other patients that have been marked as likely having received an infection from that patient. The process iterates by identifying the patients that have likely in turn received an infection from those patients that received an infection from the original patient and so on until no new patients are identified.

A method to identify a transmitted infection may comprise marking the pathogen samples identified as being transmitted infections on a phylogenic tree of sequenced pathogen samples. The phylogenic tree may be an original phylogenic tree computed in connection with the transmission determination above or it may be a recomputed phylogenic tree that accounts for transmitted infections as discussed above.

A method to identify a transmitted infection may comprise creating a plurality of phylogenic trees, where each tree is associated with a separate outbreak.

Example 6: Examples of Embodiments

A1. A computer implemented method for determining a transmission metric for related pathogens comprising:
a) providing a plurality of proximity tags for each of a plurality of objects, wherein each proximity tag comprises
   (i) a unique object identifier associated with an object, and
   (ii) a probable coordinate defining a probable location of the object within a period of time;
b) providing a plurality of pathogen tags, wherein each pathogen tag comprises a proximity tag, a unique pathogen identifier, and genomic sequence data obtained from a pathogen;
c) identifying a set of related pathogens according to a relationship between the plurality of pathogen tags, thereby providing a set of related pathogen tags;
d) determining the presence of one or more relationships between one or more of the plurality of proximity tags and one or more of the set of related pathogen tags according to probabilistic correlations, thereby providing a transmission metric comprising a subset of related proximity tags.

A1.1. The method of embodiment A1, wherein the plurality of objects are located within one or more defined regions.

A1.2. The method of A1.1, wherein the probable coordinate defines a probable location of the object within the one or more defined regions.

A2. The method of any one of embodiments A1 to A1.2, wherein the transmission metric comprises interactive nodes and edges presented on a display, each node comprising a pathogen tag or a proximity tag, and each edge comprising a probability of transmission.

A2.1. The method of any one of embodiments A1 to A2, wherein the relationship between the plurality of pathogen tags comprises a relationship between the genomic sequence data.

A2.2. The method of any one of embodiments A1 to A2.1, wherein the relationship between the plurality of pathogen tags comprises a relationship between the proximity tags.

A3. The method of any one of embodiments A1 to A2.2, wherein the period of time can be exact or probable.

A4. The method of any one of embodiments A1 to A3, wherein the probable coordinate defines an exact coordinate or a probable coordinate.

A5. The method of any one of embodiments A1 to A4, wherein the genomic sequence data comprises one or more SNP differences associated with a pathogen.

A5.1. The method of embodiments A5, wherein related pathogens of the set are identified according to a correlation between the one or more SNP differences and the period of time of a proximity tag.

A5.2. The method of embodiments A5, wherein related pathogens of the set are identified according to a correlation between the one or more SNP differences and the probable location of the object.

A5.3. The method of embodiments A5, wherein related pathogens of the set are identified according to a correlation between the one or more SNP differences and an expected mutation rate.

A6. The method of any one of embodiments A1 to A5, wherein the object is a subject or device.

A7. The method of embodiment A6, wherein the device is a medical device.

A8. The method embodiment A6, wherein subject is a human subject.

A9. The method of embodiment A8, wherein the human subject is a medical professional or a patient.

A10. The method of embodiment A9, wherein the human subject is a patient and the proximity tag associated with the patient comprises clinical information related to the patient.

A11. The method of any one of embodiments A1 to A5, wherein the coordinate is selected from a room, hallway, entry way, elevator, stairway or portion thereof.

A13. The method of any one of embodiments A1 to A5, wherein an object comprises a vehicle, or portion thereof.

A14. The method of any one of embodiments A1 to A13, wherein the pathogen tag comprises antibiotic resistance information.

A15. The method of any one of embodiments A1 to A14, wherein the genomic sequence data comprises SNP counts or SNP differences.

A16. The method of any one of embodiments A1 to A15, wherein the related pathogens are identified by a process comprising a Random Walk or weighted Markov Chains.

A17. The method of embodiment A16, wherein SNP counts are weighted.

A18. The method of embodiment A2, wherein the probabilistic correlations comprise probabilistic matches between of the probable coordinates of two or more proximity tags and the probable coordinates of one or more of the related pathogen tags.

A18.1. The method of embodiment A9, wherein the determining the presence of one or more relationships in (d) comprises determining one or more temporal relationships between one or more medical professionals, one or more patients and one or more related pathogens.

A18.2. The method of embodiment A18.1, wherein the temporal relationships comprise one or more probable intersects between two or more proximity tags.

A19. The method of any one of embodiments A1.1 to A18, wherein the one or more defined regions comprise a hospital.

A20. The method of embodiment A19, wherein the one or more defined regions comprise three or more hospitals.

A21. The method of any one of embodiments A1 to A20, wherein the identifying the set of related pathogens of (d) comprises identifying one or more of the set of related pathogens to a species level, sub-species level or strain level according to the genomic sequence data.

A22. The method of any one of embodiments A1 to A21, wherein the identifying the set of related pathogens of (d) comprises identifying one or more of the set of related pathogens to a strain level according to an antibiotic resistance.

A23. The method of any one of embodiments A1 to A22, wherein the identifying the set of related pathogens of (d) comprises MLST typing.

A24. The method of any one of embodiments A1 to A23, wherein the identifying the set of related pathogens of (d) comprises identification of gene expression signatures.

A25. The method of any one of embodiments A1 to A24, wherein one or more of the unique object identifiers are encrypted.

A26. The method of any one of embodiments A1 to A25, wherein the probable coordinate comprises a three dimensional coordinate.

A27. The method of any one of embodiments A1 to A26, wherein the identifying the set of related pathogens of (d) comprises determining pathogen growth rates.

A28. The method of any one of embodiments A1 to A27, wherein the identifying the set of related pathogens of (d) comprises determining a pathogen's closest neighbor A29. The method of any one of embodiments A1 to A28, wherein the identifying the set of related pathogens of (d) comprises determining a pathogen's mutation rate.

A30. The method of any one of embodiments A1 to A29, wherein the identifying the set of related pathogens of (d) comprises determining a pathogen evolutionary distance between two or more pathogens.

A31. The method of any one of embodiments A1 to A30, wherein the identifying the set of related pathogens of (d) comprises generating a phylogenetic metric.

A32. The method of any one of embodiments A1 to A31, wherein the set of related pathogens consists of an ESKAPE pathogen.

A33. The method of any one of embodiments A1 to A32, wherein a transmission path of related pathogens in determined according to the transmission metric.

A34. The method of embodiment A33, wherein a parent pathogen is identified according to the transmission path.

A35. The method of embodiment A33, wherein a patient zero is identified according to the transmission path.

A36. The method of embodiment A33, wherein a probable location of a related pathogen is predicted according to the transmission path.

A37. The method of any one of embodiments A1 to A36, wherein the genomic information comprises a nucleic acid sequence of an entire genome of a pathogen.

A38. The method of any one of embodiments A1 to A37, wherein the genomic information comprises a nucleic acid sequence of a portion of a genome of a pathogen.

A40. The method of any one of embodiments A9 to A37, wherein the human subject is a patient infected with a pathogen, and a proximity tag of the infected patient comprises an amount of one or more symptoms of the patient, or amount thereof.

A41. The method of any one of embodiments A9 to A40, wherein the human subject is a patient infected with a pathogen, and a proximity tag of the infected patient comprises an amount of the one or more symptoms of the infected patient.

A42. The method of embodiment A41, wherein a pathogen tag comprises a proximity tag of an infected patient.

A43. The method of any one of embodiments A40 to A42, the determining of (d) comprises a method of weighting the one or more proximity tags according to the amount of the one or more symptoms of an infected patient.

A44. The method of embodiment A43, wherein an amount of virulence of a related pathogen is determined according to the relationship determined in (d).

A45. The method of embodiment A43, wherein an amount of virulence of a related pathogen is determined according to the transmission matrix.

A46. The method of embodiment A43, wherein a patient is determined to be immunocompromised according to the transmission matrix.

B1. A non-transitory computer-readable storage medium with an executable program stored thereon, which program is configured to instruct a microprocessor to perform the method of any one of embodiments A1 to A46.

C1. A computer implemented method for determining a transmission metric for related pathogens comprising:
a) providing a plurality of proximity tags for each of a plurality of objects, wherein each proximity tag comprises
    (i) a unique object identifier associated with an object, and
    (ii) optionally, a location, or probable location of the object;
b) providing a plurality of pathogen tags, wherein each pathogen tag comprises a proximity tag, a unique pathogen identifier, and genomic sequence data obtained from a pathogen;
c) identifying a set of related pathogens according to a relationship between the plurality of pathogen tags, thereby providing a set of related pathogen tags;
d) determining the presence of one or more relationships between one or more of the plurality of proximity tags and one or more of the set of related pathogen tags according to probabilistic correlations, thereby providing a transmission metric comprising a subset of related proximity tags.

C2. The method of embodiment C1, wherein one or more of the plurality of proximity tags comprises a location, or probable location of an object associated with a proximity tag.

C3. The method of embodiment C1 or C2, wherein one or more of the plurality of proximity tags comprises time information indicating an exact or probable period of time.

C4. The method of any one of embodiments C1 to C3, wherein the location, or probable location comprises a Cartesian coordinate or a location within Euclidean space.

C5. The method of embodiment C3 or C4, wherein the time information indicates the location or probable location of an object at a particular time, or within a period of time.

C6. The method of any one of embodiments C1 to C5, wherein the transmission metric comprising a subset of related proximity tags or pathogens tags represented as nodes and a plurality of edges connecting one or more pairs of nodes.

C6.1 The method of embodiment C6, wherein each of the plurality of edges comprises the one or more relationships.

C7. The method of embodiment C6 or C6.1, wherein one or more of the plurality of edges are weighted.

C8. The method of embodiment C7, wherein the one or more edges are weighted according to genetic similarities or differences between the pathogens associated with each of a pair of nodes.

C9. The method of embodiment C8, the genetic similarities or differences comprise similarities or differences between a set of single nucleotide polymorphisms (SNPs).

C10. The method of any one of embodiments C7 to C9, wherein the one or more edges are weighted according to the location, or probable location of the proximity tag associated with each node of a pair of nodes.

C11. The method of any one of embodiments C7 to C10, wherein the one or more edges are weighted according to a distance between the location, or probable location of the proximity tag associated with each of a pair of nodes.

C12. The method of any one of embodiments C7 to C11, wherein the one or more edges are weighted according to time.

C13. The method of any one of embodiments C7 to C12, wherein the one or more edges are weighted according to genetic similarities or differences between the pathogens associated with each of a pair of nodes; the location, or probable location of the proximity tag associated with each node of a pair of nodes; and a time, or period of time associated with each node of a pair of nodes.

C14. The method of any one of embodiments C7 to C13, wherein one or more edges are normalized.

C15. The method of any one of embodiments C1 to C14, wherein related pathogens of the set are identified according to having similar nucleic acid content, similar patterns of single nucleotide variations, similar patterns of SNPs, or similar microbiological growth characteristics.

C16. The method of any one of embodiments C1 to C15, wherein related pathogens of the set are pathogens of the same species or highly related strains.

C17. The method of any one of embodiments C1 to C16, the object is a human or device.

C18. The method of any one of embodiments C1 to C17, wherein the proximity tag associated with the object comprises clinical information related to a patient.

C19. The method of any one of embodiments C7 to C17, wherein the one or more edges are weighted by a process comprising a Random Walk or weighted Markov Chains.

C20. The method of any one of embodiments C1 to C19, wherein the probabilistic correlations comprise probabilistic matches or probabilistic overlap between the location or probable location of a pair of proximity tags, a pair of pathogen tags, or a pair of nodes.

C21. The method of any one of embodiments C1 to C20, wherein the probabilistic correlations comprise probabilistic matches or probabilistic overlap between a time or period of time associated with a pair of proximity tags, a pair of pathogen tags, or a pair of nodes.

C22. The method of any one of embodiments C1 to C21, wherein the probabilistic correlations comprise probabilistic matches or probabilistic overlap between genetic variations determined for a pair of related pathogens or a pair of nodes.

C23. The method of any one of embodiments C1 to C22, wherein the determining the presence of one or more relationships in (d) comprises determining one or more temporal relationships between one or more objects.

C24. The method of any one of embodiments C1 to C23, wherein the identifying the set of related pathogens of (d) comprises generating a phylogenetic metric.

C25. The method of any one of embodiments C1 to C24, wherein a probable source of an outbreak is determined according to the transmission metric.

The examples set forth above illustrate certain embodiments and do not limit the technology.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A computer implemented method for determining a transmission path of related pathogens comprising:
    a) providing a plurality of proximity tags for each of a plurality of objects and for each of a plurality of pathogens, wherein the plurality of objects comprises at least one device and at least one human subject, and wherein each proximity tag comprises
  (i) a unique object identifier associated with an object of the plurality of objects, and
  (ii) a probable coordinate defining a location of the object within a period of time;
b) providing a plurality of pathogen tags for each of a plurality of object and for each of a plurality of pathogens, wherein each pathogen tag is associated with a proximity tag, and comprises a unique pathogen identifier, and genomic sequence data obtained from a pathogen;
c) identifying, based on the genomic sequence data for the plurality of pathogen tags, a set of two or more related pathogens according to a similarity between genomic sequence data for the plurality of pathogen tags to provide a set of related pathogen tags, wherein identifying the set of two or more related pathogens further comprises computing a number of mutational changes, wherein the computed number of mutational changes are normalized using a total number of genomic positions for which each of the set of two or more related pathogens has a base call;
d) determining the presence of one or more relationships between one or more of the plurality of proximity tags and one or more of the set of related pathogen tags according to probabilistic correlations of a probable coordinate relationship and/or temporal relationship between the one or more of the plurality of proximity tags and the one or more of the set of related pathogen tags;
e) providing a transmission metric comprising a graphical representation of a plurality of nodes and edges and the determined one or more relationships, each node comprising one of the set of related pathogen tags or one of the plurality of proximity tags, and each edge comprising a probability of transmission between two or more nodes, wherein one of the nodes comprises a first proximity tag for a first object and a second proximity tag for a second object;
wherein the graphical representation of the nodes and the edges are displayed using a display,
wherein the display is configured to receive user input,
wherein the nodes and the edges comprise an interactive node and an interactive edge,
wherein the interactive node further comprises a pathogen tag or a proximity tag, and
wherein the interactive edge further comprises a probability of transmission;
f) determining, based on the transmission metric, a transmission path of one or more of the set of related pathogens;
g) receiving one or more inputs through a user interface, wherein the one or more inputs include a user query, and wherein the user query includes a selection of at least one of one or more statistical algorithms, one or more statistical analysis algorithms, one or more statistical significance algorithms, one or more iterative steps, and one or more validation algorithms; and
h) sending instructions to execute one or more program instructions associated with the user query.

2. The method of claim 1, wherein the probable coordinate is a three-dimensional coordinate.

3. The method of claim 1, wherein the step of identifying two or more related pathogens comprises a Random Walk or weighted Markov Chains.

4. The method of claim 1, wherein the probabilistic correlations comprise probabilistic matches between the probable coordinates of two or more proximity tags and the probable coordinates of one or more of the related pathogen tags.

5. The method of claim 1, wherein the determining the presence of one or more relationships in (d) further comprises the step of determining one or more temporal relationships between one or more human subjects and one or more related pathogens.

6. The method of claim 5, wherein the temporal relationships comprise one or more probable intersects between two or more proximity tags.

7. The method of claim 1, wherein the identifying the set of related pathogens of (c) further comprises the step of identifying one or more of the set of related pathogens to a sub-species level or strain level according to the genomic sequence data.

8. The method of claim 1, wherein the identifying the set of related pathogens of (c) further comprises the step of MLST typing, identification of gene expression signatures, determining a pathogen's closest neighbor, determining a pathogen's mutation rate, or determining pathogen growth rates.

9. The method of claim 1, wherein the identifying the set of related pathogens of (c) further comprises the step of determining a pathogen's evolutionary distance between two or more other pathogens.

10. The method of claim 1, wherein the identifying the set of related pathogens of (c) further comprises the step of generating a phylogenetic metric.

11. The method of claim 1, further comprising the step of identifying a parent pathogen or a patient zero based at least in part on the transmission path.

12. The method of claim 1, further comprising the step of predicting a probable location of a related pathogen at a future time based at least in part on the transmission path.

13. The method of claim 1, wherein the human subject is a patient infected with a pathogen, and a proximity tag of the infected patient comprises the presence of, severity of or amount of one or more symptoms of the infected patient, and the determining of (d) further comprises weighting one or more proximity tags according to the presence, severity or amount of the one or more symptoms of the infected patient.

14. A non-transitory computer-readable storage medium with an executable program stored thereon, which program is configured to instruct a microprocessor to:
  a) obtain a plurality of proximity tags for each of a plurality of objects, wherein each proximity tag comprises:
    (i) a unique object identifier associated with an object of the plurality of objects, and
    (ii) a probable coordinate defining a location of the object within a period of time;
  b) obtain a plurality of pathogen tags, wherein each pathogen tag is associated with a proximity tag, and comprises a unique pathogen identifier, and genomic sequence data obtained from a pathogen;
  c) identify, based on the genomic sequence data for the plurality of pathogen tags, a set of two or more related pathogens according to a similarity between genomic sequence data for the plurality of pathogen tags to prove a set of related pathogen tags, wherein identifying the set of two or more related pathogens further comprises computing a number of mutational changes, wherein the computed number of mutational changes are normalized using a total number of genomic positions for which each of the set of two or more related pathogens has a base call;
d) determine the presence of one or more relationships between one or more of the plurality of proximity tags and one or more of the set of related pathogen tags according to probabilistic correlations of a probable coordinate relationship and/or temporal relationship between the one or more of the plurality of proximity tags and the one or more of the set of related pathogen tags;
e) generating a novel transmission metric, wherein the novel transmission metric comprises a graphical representation of a plurality of nodes and edges and the determined one or more relationships, each node comprising one of the set of related pathogen tags or one of the plurality of proximity tags, and each edge comprising a probability of transmission between two or more nodes, wherein one of the nodes comprises a first proximity tag for a first object and a second proximity tag for a second object
wherein the graphical representation of the nodes and the edges are displayed using a display,
wherein the display is configured to receive user input, wherein the nodes and the edges comprise an interactive node and an interactive edge,
wherein the interactive node further comprises a pathogen tag or a proximity tag, and
wherein the interactive edge further comprises a probability of transmission;
f) determine, based on the transmission metric, a transmission path of one or more of the set of related pathogens;
g) receive one or more inputs through a user interface, wherein the one or more inputs include a user query, and wherein the user query includes a selection of at least one of one or more statistical algorithms, one or more statistical analysis algorithms, one or more statistical significance algorithms, one or more iterative steps, and one or more validation algorithms; and
h) send instructions to execute one or more program instructions associated with the user query.

15. A computer implemented system for performing a genome analysis comprising:
one or more non-transitory computer readable storage mediums; and
one or more computer processors, wherein the computer processor is configured to:
a) provide, by the one or more computer processors, a plurality of proximity tags for each of a plurality of objects, wherein the plurality of objects comprises at least one device and at least one human subject, wherein each proximity tag comprises:
  (i) a unique object identifier associated with an object of the plurality of objects or a human subject, and
  (ii) a probable coordinate defining a location of the object or the human subject within a period of time;
b) provide, by the one or more computer processors, a plurality of pathogen tags, wherein each pathogen tag is associated with a proximity tag, and comprises a unique pathogen identifier, and genomic sequence data obtained from a pathogen;
c) identify, by the one or more computer processors, a set of two or more related pathogens according to a similarity between genomic sequence data for the plurality of pathogen tags based on the genomic sequence data for the plurality of pathogen tags to provide a set of related pathogen tags, wherein identifying the set of two or more related pathogens further comprises computing a number of mutational changes, wherein the computed number of mutational changes are normalized using a total number of genomic positions for which each of the set of two or more related pathogens has a base call;
d) determine, by the one or more computer processors, the presence of one or more relationships between one or more of the plurality of proximity tags and one or more of the set of related pathogen tags according to probabilistic correlations of a probable coordinate relationship and/or temporal relationship between the one or more of the plurality of proximity tags and the one or more of the set of related pathogen tags;
e) provide, by the one or more computer processors, a transmission metric comprising a graphical representation of a plurality of nodes and edges and the determined one or more relationships, each node comprising one of the set of related pathogen tags or one of the plurality of proximity tags, and each edge comprising a probability of transmission between two or more nodes, wherein one of the nodes comprises a first proximity tag for a first object and a second proximity tag for a second object,
wherein the graphical representation of the nodes and the edges are displayed using a display,
wherein the display is configured to receive user input, wherein the nodes and the edges comprise an interactive node and an interactive edge,
wherein the interactive node further comprises a pathogen tag or a proximity tag, and
wherein the interactive edge further comprises a probability of transmission;
f) determine, by the one or more computer processors, a transmission path of one or more of the set of related pathogens based on the transmission metric;
g) receive, by the one or more computer processors, one or more inputs through a user interface, wherein the one or more inputs include a user query, and wherein the user query includes a selection of at least one of one or more statistical algorithms, one or more statistical analysis algorithms, one or more statistical significance algorithms, one or more iterative steps, one or more validation algorithms; and
h) send, by the one or more computer processors, instructions to execute one or more program instructions associated with the user query.

* * * * *